US008674059B2

(12) United States Patent
Nakamura et al.

(10) Patent No.: US 8,674,059 B2
(45) Date of Patent: Mar. 18, 2014

(54) COLON CANCER RELATED GENE TOM34

(75) Inventors: Yusuke Nakamura, Bunkyo-ku (JP); Yoichi Furukawa, Bunkyo-ku (JP); Hideaki Tahara, Bunkyo-ku (JP); Takuya Tsunoda, Kawasaki (JP); Satoshi Matsushima, Kawasaki (JP)

(73) Assignee: Oncotherapy Science, Inc. (JP)

( * ) Notice: Subject to any disclaimer, the term of this patent is extended or adjusted under 35 U.S.C. 154(b) by 963 days.

(21) Appl. No.: 11/913,228

(22) PCT Filed: Jul. 21, 2006

(86) PCT No.: PCT/JP2006/314947
§ 371 (c)(1),
(2), (4) Date: Mar. 27, 2009

(87) PCT Pub. No.: WO2007/013576
PCT Pub. Date: Feb. 1, 2007

(65) Prior Publication Data
US 2009/0214571 A1      Aug. 27, 2009

Related U.S. Application Data

(60) Provisional application No. 60/703,265, filed on Jul. 27, 2005.

(51) Int. Cl.
*A61K 38/00*       (2006.01)
(52) U.S. Cl.
USPC .......................................................... 530/300
(58) Field of Classification Search
USPC .......................................................... 530/300
See application file for complete search history.

(56) References Cited

U.S. PATENT DOCUMENTS

| 5,539,084 | A | * | 7/1996 | Geysen | 530/334 |
| 5,785,973 | A | * | 7/1998 | Bixler et al. | 424/196.11 |
| 5,840,839 | A | * | 11/1998 | Wang et al. | 530/325 |
| 7,166,573 | B1 | | 1/2007 | Obata | |
| 7,700,359 | B2 | | 4/2010 | Chan et al. | |
| 2004/0181344 | A1 | | 9/2004 | Stephanopoulos et al. | |
| 2004/0265230 | A1 | | 12/2004 | Martinez et al. | |

FOREIGN PATENT DOCUMENTS

| WO | 01/49310 A1 | 7/2001 |
| WO | WO 2004/018667 A1 | 3/2004 |
| WO | WO 2004/061423 A2 | 7/2004 |

OTHER PUBLICATIONS

Yang et al., Arch. Biochem. Biophys., 2002, 400(1):105-110.*
Riott et al., Immunology, Fourth Edition, 1996, Mosby, p. 7.9-7.11.*
Lee et al., J. Immunol., 1999, 163:6292-6300.*
Kirkin et al., 1998, APMIS, 106 : 665-679.*
Chaux et al, Int J Cancer, 1998, 77: 538-542.*
Boon, Adv Can Res, 1992, 58:177-210.*
Celis, J of Clinical Investigation, 2002, 110:1765-1768.*
Evans et al., Q. J. Med 1999: 92: 299-307.*
Kondo et al.; "Prominent roles of secondary anchor residues in peptide binding to HLA-A24 human class 1 molecules"; 1995; *J. Immunol.*; vol. 155, No. 9, pp. 4307-4312.
Kubo et al.; "Definition of specific peptide motifs for four major HLA-A alleles"; 1994; *J. Immunol.*; vol. 152, No. 8, pp. 3913-3924.
Zaremba et al.; "Identification of an enhancer agonist cytotoxic T lymphocyte peptide from human carcinoembryonic antigen"; 1997; *Cancer Res.*; vol. 57, pp. 4750-4757.
Chewawiwat, N., et al, "Characterization of the novel mitochondrial protein import component, Tom34, in mammalian cells," *Journal of Biochemistry*, vol. 125(4), pp. 721-727 (Apr. 4, 1999).
Mukhopadhyay, A., et al., "Tom34 unlike Tom20 does not interact with the leader sequences of mitochondrial precursor proteins," *Archives of Biochemistry and Biophysics*, vol. 400(1), pp. 97-104 (Apr. 1, 2002).
Shimokawa, T., et al, "Identification of TOMM34, which shows elevated expression in the majority of human colon cancers, as a novel drug target," *International Journal of Oncology*, vol. 29(2), pp. 381-386 (Aug. 2006).
Terada, K., et al., "Expression of Tom43 splicing isoforms in mouse testis and knockout of Tom34 in mice," *Journal of Biochemistry* (Tokyo), vol. 133(5), pp. 625-631 (May 2003).
Chen, et al., "Response of a human T cell clone to a large panel of altered peptide ligands carrying single residue substitutions in an antigenic peptide: characterization and frequencies of TCR agonism and TCR antagonism with or without partial activation," *J. Immunol.* vol. 157(9), pp. 3783-3790 (Nov. 1, 1996).
Ida, et al., "Crisscross CTL Induction by SYT-SSX Junction Peptide and Its HLA-A*2402 Anchor Substitute," *J. Immunol.*, vol. 173(2), pp. 1436-1443 (Jul. 15, 2004).
Kalejs, et al., "Cancer/testis antigens and gametogenesis: a review and "brain-storming" session," *Cancer Cell International* vol. 5: 4, 11 pgs. (2005).
Okuno, K., et al., "Phasse I clinical trial of a novel peptide vaccine in combination with UFT/LV for metastatic colorectal cancer, "*Experimental and Therapeutic Medicine*, vol. 2(1), pp. 73-79 (2011).
U.S. Appl. No. 13/990,766, which is a U.S. National Stage of PCT/JP2011/006551, filed Nov. 25, 2011, 73 pages.
Indian Office Action issued on Nov. 19, 2013 for Indian Patent Application No. 954/CHENP/2008, filed Feb. 26, 2008.
Fisenko, et al., Handbook on experimental (preclinical) studies of new pharmacological substances, Moscow, 2000, pp. 257-263, with Engliash Translation, 28 pages.
Fisenko, et al., Handbook on experimental (preclinical) studies of new pharmacological substances, Moscow, 2000, pp. 319-334, with English Translation, 61 pages.

* cited by examiner

*Primary Examiner* — Hong Sang
(74) *Attorney, Agent, or Firm* — Kilpatrick Townsend & Stockton LLP

(57) ABSTRACT

Objective methods for detecting and diagnosing colon cancer are described herein. In one embodiment, the diagnostic method involves determining the expression level of TOM34 that discriminates between colon cancer cells and normal cells. Finally, the present invention provides methods of screening for therapeutic agents useful in the treatment of colon cancer, methods of treating colon cancer and method for vaccinating a subject against colon cancer.

1 Claim, 10 Drawing Sheets

☐ Peptide +
■ Peptide −

Target : TISI with peptide pulse

SEQUENCE LISTING

<160> NUMBER OF SEQ ID NOS: 65

<210> SEQ ID NO 1
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 1

Thr Tyr Ser Asn Arg Ala Leu Cys Tyr Leu
1               5                   10

<210> SEQ ID NO 2
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 2

Leu Tyr Ser Asn Arg Ala Ala Cys His Leu
1               5                   10

<210> SEQ ID NO 3
<211> LENGTH: 10
<212> TYPE: PRT
<213> ORGANISM: Artificial
<220> FEATURE:
<223> OTHER INFORMATION: synthetic peptide HLA-Class I (HLA-A24)
      epitope candidate 10-mer

<400> SEQUENCE: 3

Ala Tyr Glu Ala Lys Glu Lys Tyr Pro Met
1               5                   10

<210> SEQ ID NO 4
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 4

Arg Val Leu Lys Glu Glu Gly Asn Glu Leu
1               5                   10

<210> SEQ ID NO 5
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 5

Lys Tyr Ser Glu Ser Leu Leu Cys Ser Asn
1               5                   10

<210> SEQ ID NO 6
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 6

Lys Ala Ile Glu Lys Tyr Ser Glu Ser Leu
1               5                   10

<210> SEQ ID NO 7
<211> LENGTH: 10
<212> TYPE: PRT
<213> ORGANISM: Artificial
<220> FEATURE:
<223> OTHER INFORMATION: synthetic peptide HLA-Class I (HLA-A24) epitope -continued candidate 10-mer, TOM34-299 decapeptide, HLA-A24
restricted epitope peptide

<400> SEQUENCE: 7

Lys Leu Arg Gln Glu Val Lys Gln Asn Leu
1               5                   10

<210> SEQ ID NO 8
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 8

Arg Met Thr Arg Ala Leu Met Asp Ser Leu
1               5                   10

<210> SEQ ID NO 9
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 9

Gln Tyr Thr Glu Ala Val Lys Asp Cys Thr
1               5                   10

<210> SEQ ID NO 10
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 10

Leu Val Pro Phe Ser Ile Lys Pro Leu Leu
1               5                   10

<210> SEQ ID NO 11
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 11

Lys Ser Ser Phe Ala Asp Ile Ser Asn Leu
1               5                   10

<210> SEQ ID NO 12
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 12

Tyr Ser Glu Ser Leu Leu Cys Ser Asn Leu
1               5                   10

<210> SEQ ID NO 13

```
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 13

Ala Leu Val Pro Phe Ser Ile Lys Pro Leu
1               5                   10

<210> SEQ ID NO 14
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 14

Ser Ser Phe Ala Asp Ile Ser Asn Leu Leu
1               5                   10

<210> SEQ ID NO 15
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 15

Asp Cys Ile Lys Asp Cys Thr Ser Ala Leu
1               5                   10

<210> SEQ ID NO 16
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 16

Ala Ile Glu Lys Tyr Ser Glu Ser Leu Leu
1               5                   10

<210> SEQ ID NO 17
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 17

Glu Ala Val Lys Asp Cys Thr Glu Ala Leu
1               5                   10

<210> SEQ ID NO 18
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 18

Asn Gly Gln Tyr Ala Glu Ala Ser Ala Leu
```

```
<210> SEQ ID NO 19
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 19

Glu Gly Ile Asn Arg Met Thr Arg Ala Leu
 1               5                  10

<210> SEQ ID NO 20
<211> LENGTH: 10
<212> TYPE: PRT
<213> ORGANISM: Artificial
<220> FEATURE:
<223> OTHER INFORMATION: synthetic peptide HLA-Class I (HLA-A24) epitope
      candidate 10-mer

<400> SEQUENCE: 20

Lys Ala Leu Lys Asp Tyr Lys Ser Ser Phe
 1               5                  10

<210> SEQ ID NO 21
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 21

Ala Tyr Val Asp Tyr Lys Thr Val Leu
 1               5

<210> SEQ ID NO 22
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 22

Leu Tyr Gly Arg Ala Leu Arg Val Leu
 1               5

<210> SEQ ID NO 23
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 23

Lys Phe Pro Asp Ser Val Glu Glu Leu
 1               5

<210> SEQ ID NO 24
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer
```

```
<400> SEQUENCE: 24

Asp Tyr Lys Ser Ser Phe Ala Asp Ile
1               5

<210> SEQ ID NO 25
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 25

Ser Phe Ala Asp Ile Ser Asn Leu Leu
1               5

<210> SEQ ID NO 26
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 26

Lys Tyr Pro Met Ala Tyr Val Asp Tyr
1               5

<210> SEQ ID NO 27
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 27

Lys Tyr Ser Glu Ser Leu Leu Cys Ser
1               5

<210> SEQ ID NO 28
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 28

Cys Tyr Leu Val Leu Lys Gln Tyr Thr
1               5

<210> SEQ ID NO 29
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 29

Arg Leu Lys Leu Pro Ser Ile Pro Leu
1               5

<210> SEQ ID NO 30
<211> LENGTH: 9
<212> TYPE: PRT
```

```
<213> ORGANISM: Artificial
<220> FEATURE:
<223> OTHER INFORMATION: synthetic peptide HLA-Class I (HLA-A24) epitope
      candidate 9-mer

<400> SEQUENCE: 30

Leu Gly Pro Glu Trp Arg Leu Lys Leu
1               5

<210> SEQ ID NO 31
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 31

Ser Ala Gln Lys Arg Trp Asn Ser Leu
1               5

<210> SEQ ID NO 32
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 32

Val Leu Lys Glu Glu Gly Asn Glu Leu
1               5

<210> SEQ ID NO 33
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 33

Gln Tyr Thr Glu Ala Val Lys Asp Cys
1               5

<210> SEQ ID NO 34
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 34

Asp Ser Leu Gly Pro Glu Trp Arg Leu
1               5

<210> SEQ ID NO 35
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 35

Gln Tyr Ala Glu Ala Ser Ala Leu Tyr
1               5
```

-continued

<210> SEQ ID NO 36
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 36

Tyr Ser Asn Arg Ala Ala Cys His Leu
1               5

<210> SEQ ID NO 37
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 37

Leu Val Pro Phe Ser Ile Lys Pro Leu
1               5

<210> SEQ ID NO 38
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 38

Tyr Ser Asn Arg Ala Leu Cys Tyr Leu
1               5

<210> SEQ ID NO 39
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 39

Gly Ile Asn Arg Met Thr Arg Ala Leu
1               5

<210> SEQ ID NO 40
<211> LENGTH: 9
<212> TYPE: PRT
<213> ORGANISM: Artificial
<220> FEATURE:
<223> OTHER INFORMATION: synthetic peptide HLA-Class I (HLA-A24) epitope
      candidate 9-mer

<400> SEQUENCE: 40

Ala Ile Glu Lys Tyr Ser Glu Ser Leu
1               5

<210> SEQ ID NO 41
<211> LENGTH: 22
<212> TYPE: DNA
<213> ORGANISM: Artificial
<220> FEATURE:
<223> OTHER INFORMATION: synthetic RT-PCR amplification primer for GAPDH
      quantitative control

<400> SEQUENCE: 41
acaacagcct caagatcatc ag                                              22

<210> SEQ ID NO 42
<211> LENGTH: 20
<212> TYPE: DNA
<213> ORGANISM: Artificial
<220> FEATURE:
<223> OTHER INFORMATION: synthetic RT-PCR amplification primer for GAPDH
      quantitative control

<400> SEQUENCE: 42
ggtccaccac tgacacgttg                                                 20

<210> SEQ ID NO 43
<211> LENGTH: 23
<212> TYPE: DNA
<213> ORGANISM: Artificial
<220> FEATURE:
<223> OTHER INFORMATION: synthetic RT-PCR amplification primer for
      TOM34, TOM34 specific primer

<400> SEQUENCE: 43
tggtataaac ctaaggccct gat                                             23

<210> SEQ ID NO 44
<211> LENGTH: 23
<212> TYPE: DNA
<213> ORGANISM: Artificial
<220> FEATURE:
<223> OTHER INFORMATION: synthetic RT-PCR amplification primer for
      TOM34, TOM34 specific primer, RT-PCR primer for TOM34 probe

<400> SEQUENCE: 44
taaacagctt aggtgcctct ctg                                             23

<210> SEQ ID NO 45
<211> LENGTH: 22
<212> TYPE: DNA
<213> ORGANISM: Artificial
<220> FEATURE:
<223> OTHER INFORMATION: synthetic RT-PCR primer for TOM34 probe

<400> SEQUENCE: 45
gaacgtgaag gcattctaca ga                                              22

<210> SEQ ID NO 46
<211> LENGTH: 51
<212> TYPE: DNA
<213> ORGANISM: Artificial
<220> FEATURE:
<223> OTHER INFORMATION: synthetic oligonucleotide for preparation of
      psiU6BX plasmid vector for siD, TOM34 siD position
      288-306 insert sequence

<400> SEQUENCE: 46
caccgaaagt gttctctact ccattcaaga gatggagtag agaacacttt c              51

<210> SEQ ID NO 47
<211> LENGTH: 51
<212> TYPE: DNA
<213> ORGANISM: Artificial
<220> FEATURE:
<223> OTHER INFORMATION: synthetic oligonucleotide for preparation of
      psiU6BX plasmid vector for siD, TOM34 siD position
      288-306 insert sequence

<400> SEQUENCE: 47

```
aaaagaaagt gttctctact ccatctcttg aatggagtag agaacactttt c         51
```

<210> SEQ ID NO 48
<211> LENGTH: 19
<212> TYPE: DNA
<213> ORGANISM: Artificial
<220> FEATURE:
<223> OTHER INFORMATION: synthetic target sequence for TOM34 siD siRNA
      position 288-306

<400> SEQUENCE: 48

```
gaaagtgttc tctactcca                                              19
```

<210> SEQ ID NO 49
<211> LENGTH: 47
<212> TYPE: DNA
<213> ORGANISM: Artificial
<220> FEATURE:
<223> OTHER INFORMATION: synthetic hairpin siRNA for TOM34 siD siRNA
      position 288-306

<400> SEQUENCE: 49

```
gaaagtgttc tctactccat tcaagagatg gagtagagaa cactttc               47
```

<210> SEQ ID NO 50
<211> LENGTH: 51
<212> TYPE: DNA
<213> ORGANISM: Artificial
<220> FEATURE:
<223> OTHER INFORMATION: synthetic oligonucleotide for preparation of
      psiU6BX plasmid vector for siE, TOM34 siE position
      329-347 insert sequence

<400> SEQUENCE: 50

```
caccggatgg aaactgcaga gacttcaaga gagtctctgc agtttccatc c          51
```

<210> SEQ ID NO 51
<211> LENGTH: 51
<212> TYPE: DNA
<213> ORGANISM: Artificial
<220> FEATURE:
<223> OTHER INFORMATION: synthetic oligonucleotide for preparation of
      psiU6BX plasmid vector for siE, TOM34 siE position
      329-347 insert sequence

<400> SEQUENCE: 51

```
aaaaggatgg aaactgcaga gactctcttg aagtctctgc agtttccatc c          51
```

<210> SEQ ID NO 52
<211> LENGTH: 19
<212> TYPE: DNA
<213> ORGANISM: Artificial
<220> FEATURE:
<223> OTHER INFORMATION: synthetic target sequence for TOM34 siE siRNA
      position 329-347

<400> SEQUENCE: 52

```
ggatggaaac tgcagagac                                              19
```

<210> SEQ ID NO 53
<211> LENGTH: 47
<212> TYPE: DNA
<213> ORGANISM: Artificial
<220> FEATURE:
<223> OTHER INFORMATION: synthetic hairpin siRNA for TOM34 siE siRNA
      position 329-347

<400> SEQUENCE: 53
ggatggaaac tgcagagact tcaagagagt ctctgcagtt tccatcc            47

<210> SEQ ID NO 54
<211> LENGTH: 51
<212> TYPE: DNA
<213> ORGANISM: Artificial
<220> FEATURE:
<223> OTHER INFORMATION: synthetic oligonucleotide for preparation of
      psiU6BX plasmid vector for EGFP control insert sequence

<400> SEQUENCE: 54
caccgaagca gcacgacttc ttcttcaaga gagaagaagt cgtgctgctt c        51

<210> SEQ ID NO 55
<211> LENGTH: 51
<212> TYPE: DNA
<213> ORGANISM: Artificial
<220> FEATURE:
<223> OTHER INFORMATION: synthetic oligonucleotide for preparation of
      psiU6BX plasmid vector for EGFP control insert sequence

<400> SEQUENCE: 55
aaaagaagca gcacgacttc ttctctcttg aagaagaagt cgtgctgctt c        51

<210> SEQ ID NO 56
<211> LENGTH: 19
<212> TYPE: DNA
<213> ORGANISM: Artificial
<220> FEATURE:
<223> OTHER INFORMATION: synthetic target sequence for EGFP control

<400> SEQUENCE: 56
gaagcagcac gacttcttc                                            19

<210> SEQ ID NO 57
<211> LENGTH: 47
<212> TYPE: DNA
<213> ORGANISM: Artificial
<220> FEATURE:
<223> OTHER INFORMATION: synthetic hairpin siRNA for EGFP control

<400> SEQUENCE: 57
gaagcagcac gacttcttct ctcttgaaga agaagtcgtg ctgcttc             47

<210> SEQ ID NO 58
<211> LENGTH: 29
<212> TYPE: DNA
<213> ORGANISM: Artificial
<220> FEATURE:
<223> OTHER INFORMATION: synthetic RT-PCR amplification primer for TOM34
      coding region

<400> SEQUENCE: 58
cataagcttg catggccccc aaattccca                                 29

<210> SEQ ID NO 59
<211> LENGTH: 23
<212> TYPE: DNA
<213> ORGANISM: Artificial
<220> FEATURE:
<223> OTHER INFORMATION: synthetic RT-PCR amplification primer for TOM34
      coding region

<400> SEQUENCE: 59
gttaagcttt tagtgtaggt tct                                       23

<210> SEQ ID NO 60

-continued

```
<211> LENGTH: 2205
<212> TYPE: DNA
<213> ORGANISM: Homo sapiens
<220> FEATURE:
<221> NAME/KEY: CDS
<222> LOCATION: (141)..(1070)
<223> OTHER INFORMATION: human 34kDa-translocase of the outer
      mitochondrial membrane (TOM34, TOMM34, URCC3)

<400> SEQUENCE: 60
aggtctcgca ggccccgccc cctcgccgcg ggttcgctgt tgggcggaga tattcgccgc      60
cggcgcttgc gcccggaagg tgtgccgcac cacacggggg aggaaggaag gagctcccaa     120
ctcgccggcc tggccacggg atg gcc ccc aaa ttc cca gac tct gtg gag gag    173
                      Met Ala Pro Lys Phe Pro Asp Ser Val Glu Glu
                        1               5                  10 ctc cgc gcc gcc ggc aat gag agt ttc cgc aac ggc cag tac gcc gag      221
Leu Arg Ala Ala Gly Asn Glu Ser Phe Arg Asn Gly Gln Tyr Ala Glu
                 15                  20                  25 gcc tcc gcg ctc tac ggc cgc gcg ctg cgg gtg ctg cag gcg caa ggt      269
Ala Ser Ala Leu Tyr Gly Arg Ala Leu Arg Val Leu Gln Ala Gln Gly
         30                  35                  40 tct tca gac cca gaa gaa gaa agt gtt ctc tac tcc aac cga gca gca      317
Ser Ser Asp Pro Glu Glu Glu Ser Val Leu Tyr Ser Asn Arg Ala Ala
 45                  50                  55 tgt cac ttg aag gat gga aac tgc aga gac tgc atc aaa gat tgc act      365
Cys His Leu Lys Asp Gly Asn Cys Arg Asp Cys Ile Lys Asp Cys Thr
 60                  65                  70                  75 tca gca ctg gcc ttg gtt ccc ttc agc att aag ccc ctg ctg cgg cga      413
Ser Ala Leu Ala Leu Val Pro Phe Ser Ile Lys Pro Leu Leu Arg Arg
                 80                  85                  90 gca tct gct tat gag gct ctg gag aag tac cct atg gcc tat gtt gac      461
Ala Ser Ala Tyr Glu Ala Leu Glu Lys Tyr Pro Met Ala Tyr Val Asp
         95                 100                 105 tat aag act gtg ctg cag att gat gat aat gtg acg tca gcc gta gaa      509
Tyr Lys Thr Val Leu Gln Ile Asp Asp Asn Val Thr Ser Ala Val Glu
        110                 115                 120 ggc atc aac aga atg acc aga gct ctc atg gac tcg ctt ggg cct gag      557
Gly Ile Asn Arg Met Thr Arg Ala Leu Met Asp Ser Leu Gly Pro Glu
125                 130                 135 tgg cgc ctg aag ctg ccc tca atc ccc ttg gtg cct gtt tca gct cag      605
Trp Arg Leu Lys Leu Pro Ser Ile Pro Leu Val Pro Val Ser Ala Gln
140                 145                 150                 155 aag agg tgg aat tcc ttg cct tcg gag aac cac aaa gag atg gct aaa      653
Lys Arg Trp Asn Ser Leu Pro Ser Glu Asn His Lys Glu Met Ala Lys
                160                 165                 170 agc aaa tcc aaa gaa acc aca gct aca aag aac aga gtg cct tct gct      701
Ser Lys Ser Lys Glu Thr Thr Ala Thr Lys Asn Arg Val Pro Ser Ala
        175                 180                 185 ggg gat gtg gag aaa gcc aga gtt ctg aag gaa gaa ggc aat gag ctt      749
Gly Asp Val Glu Lys Ala Arg Val Leu Lys Glu Glu Gly Asn Glu Leu
        190                 195                 200 gta aag aag gga aac cat aag aaa gct att gag aag tac agt gaa agc      797
Val Lys Lys Gly Asn His Lys Lys Ala Ile Glu Lys Tyr Ser Glu Ser
205                 210                 215 ctc ttg tgt agt aac ctg gaa tct gcc acg tac agc aac aga gca ctc      845
Leu Leu Cys Ser Asn Leu Glu Ser Ala Thr Tyr Ser Asn Arg Ala Leu
220                 225                 230                 235 tgc tat ttg gtc ctg aag cag tac aca gaa gca gtg aag gac tgc aca      893
Cys Tyr Leu Val Leu Lys Gln Tyr Thr Glu Ala Val Lys Asp Cys Thr
                240                 245                 250 gaa gcc ctc aag ctg gat gga aag aac gtg aag gca ttc tac aga cgg      941
```

-continued

```
Glu Ala Leu Lys Leu Asp Gly Lys Asn Val Lys Ala Phe Tyr Arg Arg
            255                 260                 265 gct caa gcc cac aaa gca ctc aag gac tat aaa tcc agc ttt gca gac       989
Ala Gln Ala His Lys Ala Leu Lys Asp Tyr Lys Ser Ser Phe Ala Asp
        270                 275                 280 atc agc aac ctc cta cag att gag cct agg aat ggt cct gca cag aag      1037
Ile Ser Asn Leu Leu Gln Ile Glu Pro Arg Asn Gly Pro Ala Gln Lys
    285                 290                 295 ttg cgg cag gaa gtg aag cag aac cta cac taa aaaccca acagggcaac      1087
Leu Arg Gln Glu Val Lys Gln Asn Leu His
300                 305 tggaacccct gcctgacctt acccagagaa gccatgggcc acctgctctg tgcccgctcc    1147
tgaaacccag catgccccaa gtgagctctg aagccccctc ctcaatccct tgatggcctc    1207
ccaccctgta agaggctttg cttgttcaaa ttaaactcag tgtagtcaaa cacagacatg    1267
gttgttgcac cagaaaggtc cccactagag ctaagcgtga agctgaagct ctgtccctat    1327
tcccccagcc cagctagctg atcacaccaa cagatcctca tcagcaaagc atttggcttt    1387
gtcctgccca gtgggctgc agactgagtg ctgcccttgt agcttcccca gaccccaact    1447
cactgcagtt catctgaaca acctgagctc ctgggccggg gtggaaggag gggataaaac    1507
ctaaggccct gatccaaagc agcctgttga gctggttctc cagggctgca gtctctccag    1567
gtgtacagct gctgtccctg ccctgtcctg tccttgcaca gtctcctatg tctgagcccc    1627
agtgccttct gttcgggccc tcctttggtg ggaaggcaga gccctgaccc ttgaatggtt    1687
gtccttgact ctgtgctgct gccttctgca gagaggcacc taagctgttt aaagagccca    1747
gtgattgtgg ctgctcctcc tagaggtggg aggggcaag aggcctcctt ggtcagtgtc    1807
catgctttct gggcagggac ttggttttt gttccaacag tggccttctc cgggcttcat    1867
agttctttgt aatatgttga agttaatttg aattgactga ttttgttgaa ctgtgtgttt    1927
aagctgttgc attaaaaagc tttcttctac atcaatatct gctgtgcttt catttatgcc    1987
ttttcagctt tgcacctgga actctgtagt aataataaaa gttattgctt attgggcatt    2047
caatttgaat tgactgattt tgttgaactg tgtgtttaag ctgttgcatt aaaaagcttt    2107
cttctacatc aatatctgct gtgctttcat ttatgccttt tcagctttgc acctggaact    2167
ctgtagtaat aataaaagtt attgcttatt gggcattc                             2205

<210> SEQ ID NO 61
<211> LENGTH: 309
<212> TYPE: PRT
<213> ORGANISM: Homo sapiens
<220> FEATURE:
<223> OTHER INFORMATION: human 34kDa-translocase of the outer
      mitochondrial membrane (TOM34, TOMM34, URCC3)

<400> SEQUENCE: 61

Met Ala Pro Lys Phe Pro Asp Ser Val Glu Glu Leu Arg Ala Ala Gly
1               5                   10                  15

Asn Glu Ser Phe Arg Asn Gly Gln Tyr Ala Glu Ala Ser Ala Leu Tyr
            20                  25                  30

Gly Arg Ala Leu Arg Val Leu Gln Ala Gln Gly Ser Ser Asp Pro Glu
        35                  40                  45

Glu Glu Ser Val Leu Tyr Ser Asn Arg Ala Ala Cys His Leu Lys Asp
    50                  55                  60

Gly Asn Cys Arg Asp Cys Ile Lys Asp Cys Thr Ser Ala Leu Ala Leu
65                  70                  75                  80

Val Pro Phe Ser Ile Lys Pro Leu Leu Arg Arg Ala Ser Ala Tyr Glu
```

```
                        85                  90                  95
Ala Leu Glu Lys Tyr Pro Met Ala Tyr Val Asp Tyr Lys Thr Val Leu
                100                 105                 110

Gln Ile Asp Asp Asn Val Thr Ser Ala Val Glu Gly Ile Asn Arg Met
            115                 120                 125

Thr Arg Ala Leu Met Asp Ser Leu Gly Pro Glu Trp Arg Leu Lys Leu
        130                 135                 140

Pro Ser Ile Pro Leu Val Pro Val Ser Ala Gln Lys Arg Trp Asn Ser
145                 150                 155                 160

Leu Pro Ser Glu Asn His Lys Glu Met Ala Lys Ser Lys Ser Lys Glu
                165                 170                 175

Thr Thr Ala Thr Lys Asn Arg Val Pro Ser Ala Gly Asp Val Glu Lys
            180                 185                 190

Ala Arg Val Leu Lys Glu Glu Gly Asn Glu Leu Val Lys Lys Gly Asn
        195                 200                 205

His Lys Lys Ala Ile Glu Lys Tyr Ser Glu Ser Leu Leu Cys Ser Asn
    210                 215                 220

Leu Glu Ser Ala Thr Tyr Ser Asn Arg Ala Leu Cys Tyr Leu Val Leu
225                 230                 235                 240

Lys Gln Tyr Thr Glu Ala Val Lys Asp Cys Thr Glu Ala Leu Lys Leu
                245                 250                 255

Asp Gly Lys Asn Val Lys Ala Phe Tyr Arg Arg Ala Gln Ala His Lys
            260                 265                 270

Ala Leu Lys Asp Tyr Lys Ser Ser Phe Ala Asp Ile Ser Asn Leu Leu
        275                 280                 285

Gln Ile Glu Pro Arg Asn Gly Pro Ala Gln Lys Leu Arg Gln Glu Val
    290                 295                 300

Lys Gln Asn Leu His
305

<210> SEQ ID NO 62
<211> LENGTH: 10
<212> TYPE: PRT
<213> ORGANISM: Artificial
<220> FEATURE:
<223> OTHER INFORMATION: synthetic substituted decapeptide with high HLA
      antigen binding affinity and high cytotoxic T cell (CTL)
      inducibility
<220> FEATURE:
<221> NAME/KEY: VARIANT
<222> LOCATION: (2)..(2)
<223> OTHER INFORMATION: Xaa = Leu, Phe, Tyr, Met or Trp
<220> FEATURE:
<221> NAME/KEY: VARIANT
<222> LOCATION: (10)..(10)
<223> OTHER INFORMATION: Xaa = Phe, Leu, Ile, Trp or Met

<400> SEQUENCE: 62

Lys Xaa Arg Gln Glu Val Lys Gln Asn Xaa
1               5                   10

<210> SEQ ID NO 63
<211> LENGTH: 61
<212> TYPE: RNA
<213> ORGANISM: Artificial
<220> FEATURE:
<223> OTHER INFORMATION: synthetic exemplary hairpin TOM34 siRNA siD
<220> FEATURE:
<221> NAME/KEY: modified_base
<222> LOCATION: (20)..(42)
<223> OTHER INFORMATION: n = g, a, c or u, n at positions 23 to 42 may
      be present or absent
```

-continued

```
<400> SEQUENCE: 63
gaaaguguuc ucuacuccan nnnnnnnnnn nnnnnnnnnn nnuggaguag agaacacuuu    60
c                                                                   61

<210> SEQ ID NO 64
<211> LENGTH: 61
<212> TYPE: RNA
<213> ORGANISM: Artificial
<220> FEATURE:
<223> OTHER INFORMATION: synthetic exemplary hairpin TOM34 siRNA siE
<220> FEATURE:
<221> NAME/KEY: modified_base
<222> LOCATION: (20)..(42)
<223> OTHER INFORMATION: n = g, a, c or u, n at positions 23 to 42 may
      be present or absent

<400> SEQUENCE: 64
ggauggaaac ugcagagacn nnnnnnnnnn nnnnnnnnnn nngucucugc aguuuccauc    60
c                                                                   61

<210> SEQ ID NO 65
<211> LENGTH: 18
<212> TYPE: DNA
<213> ORGANISM: Artificial
<220> FEATURE:
<223> OTHER INFORMATION: synthetic reverse transcription oligo(dT)-12-18
      primer
<220> FEATURE:
<221> NAME/KEY: modified_base
<222> LOCATION: (13)..(18)
<223> OTHER INFORMATION: t at positions 13 to 18 may be present or
      absent

<400> SEQUENCE: 65
tttttttttt tttttttt                                                 18
```

COLON CANCER RELATED GENE TOM34

CROSS-REFERENCES TO RELATED APPLICATIONS

This application is a U.S. National Stage Application of PCT/JP2006/314947, filed Jul. 21, 2006, which claims the benefit of U.S. Provisional Application Serial No. 60/703,265 filed Jul. 27, 2005, all of which are hereby incorporated by reference in their entirety.

FIELD OF THE INVENTION

The present invention relates to methods of detecting and diagnosing colon cancer as well as methods of treating and preventing colon cancer.

BACKGROUND OF THE INVENTION

Colorectal cancer is one of the most common causes of cancer-death worldwide. Despite various advances in diagnosis and treatment of colorectal cancers, many patients with advanced colorectal cancer result in high mortality. To improve their prognosis, development of sensitive and specific diagnostic biomarkers for the detection of early-stage carcinomas and that of more effective and less harmful therapeutic drugs are desired. To attain this end, it is requisite to better understand the molecular mechanisms of colorectal carcinogenesis. Recent molecular studies have revealed that colorectal carcinogenesis involves an accumulation of genetic alternations that include genetic changes in tumor suppressor genes and/or oncogenes including APC, p53, beta-catenin and K-ras (Nishisho I, et al. Science 253: 665-669, 1991; Baker S J, et al., Science 244: 217-221, 1989; Morin P J, et al., Science 275: 1787-1790, 1997; Forrester K, et al., Nature 327: 298-303, 1987). In addition to these types of changes, epigenetic events such as altered methylation (Jones P A & Laird P W, Nat Genet 21: 163-167, 1999) and loss of imprinting (Cui H, et al., Nat Med 4: 1276-1280, 1998), and/or deregulated transcriptional control by genetic changes or other unknown mechanism(s) are involved in the genesis of colorectal tumors. Among the genes involved in carcinogenesis, we can expect that inhibition of gene products essential for proliferation and/or survival of cancer cells will result in their growth inhibition or cell death. Therefore, molecules that exert oncogenic activity and are specifically expressed in cancer cells represent promising targets for developing novel anti-cancer drugs.

Human TOM34 was discovered from human EST and cDNA databases, and predicted as a component of the mitochondrial protein import machinery, since the predicted protein shares sequence homology in the region of a 62-residue motif with known yeast Tom70 family of mitochondrial receptors (Nuttall S D, et al., DNA Cell Biol 16: 1067-1074, 1997). However, recent study disclosed that TOM34 is included mainly in the cytosolic fraction and partly in the mitochondrial and membrane fraction after fractionation of tissues and cells (Chewawiwat N, et al., J Biochem (Tokyo) 125: 721-727, 1999). Another study showed its subcellular localization in cytoplasm of HeLa cells by immunohistochemical staining (Chun-Song Yand Henry Y., Archives of Biochemistry and Biophysics 400: 105-110, 2002; Abhijit M, et al., Archives of Biochemistry and Biophysics 400: 97-104, 2002). Yeast two-hybrid screening system has shown that of TOM34 interacts in vitro with Valosin-containing protein (VCP), an AAA (ATPases associated with a variety of cellular activities) family member (Chun-Song Y, et al., Archives of Biochemistry and Biophysics 400: 105-110, 2002), or 90-kDa heat shock protein (hsp90) (Young J C, et al., J Biol Chem 273: 18007-18010, 1998). However, biological role of TOM34 remains unresolved.

It has been demonstrated that CD8+ cytotoxic T lymphocytes (CTLs) recognize epitope peptides derived from tumour-associated antigens (TAAs) presented on MHC Class I molecule, and lyse the tumor cells. Since the discovery of MAGE family as the first example of TAAs, many other TAAs have been discovered using immunological approaches (Boon T., Int J Cancer. 1993; 54(2):177-80., Boon T & van der Bruggen P, J Exp Med. 1996; 183(3):725-9., van der Bruggen P, et. al., Science. 1991; 254(5038):1643-7., Brichard V, et. al., J Exp Med. 1993; 178(2):489-95., Kawakami Y, et. al., J Exp Med. 1994; 180(1):347-52), and some of them have now been in the process of clinical development as targets of immunotherapy. TAAs discovered so far include MAGE (van der Bruggen P, et. al., Science. 1991; 254(5038):1643-7), gp100 (Kawakami Y, et. al., J Exp Med. 1994; 180(1):347-52), SART (Shichijo S, et. al., J Exp Med. 1998; 187(3):277-88), NY-ESO-1 (Chen Y T, et. al., Proc Natl Acad Sci USA. 1997; 94(5): 1914-8). At the same time, the gene products, which have been already shown to be over expressed somewhat specifically by the tumor cells, have been shown to be recognized as targets for cellular immune responses. These include p53 (Umano Y, et. al., Br J Cancer. 2001; 84(8):1052-7), HER2/neu (Tanaka H, et. al., Br J Cancer. 2001; 84(1):94-9), CEA (Nukaya I, et. al., Int J Cancer. 1999; 80(1):92-7) and others.

Although these are examples of the significant progress that have been made in the basic and clinical research (Rosenberg S A, et. al., Nat Med. 1998; 4(3):321-7., Mukherji B, et. al., Proc Natl Acad Sci USA. 1995; 92(17):8078-82., Hu X, et. al., Cancer Res. 1996; 56(11):2479-83), there are very limited number of candidate TAAs in general for treatment of adenocarcinomas including colon cancer. If there are TAAs which are abundantly expressed only in cancer cells but not in normal cells, they would be promising candidates for immunotherapeutic targets.

SUMMARY OF THE INVENTION

To verify the molecular role in colorectal carcinogenesis and find novel therapeutic targets for colorectal carcinoma (CRC) patients, we have performed expression profiles using a cDNA microarray consisting of 23040 genes (Lin Y M, et al., Oncogene 21: 4120-4128, 2002). Among the genes showing up-regulated expression in colorectal tumors, we have focused on TOM34 (34kDa-Translocase of the outer mitochondrial membrane), because its expression levels were frequently enhanced in 16 of 20 CRC samples examined. Multiple tissue northern blotting analysis revealed that this gene was abundantly expressed in the testis and ovary, and weakly in the prostate, spleen and colon but not in any of 11 other normal adult tissues examined. Immunohistochemical staining of TOM34 showed significant accumulation in CRC tissues compared with their corresponding non-cancerous mucosae.

In the present invention, it was confirmed that human TOM34 is frequently up-regulated in CRCs, and that it is expressed in the testis and the ovary but not in other 15 normal adults tissues examined. Since suppression of this TOM34 by siRNA markedly reduced the growth of colon cancer cells, the gene product may be a potential therapeutic target for human tumors as well as a useful diagnostic marker.

Furthermore, it was considered that TOM34 might serve as a TAA (Tumor Associated Antigen) which could induce significant cellular immune response against colon cancer. To examine this hypothesis, we stimulated PBMC harvested from healthy volunteers with peptides derived from TOM34 and successfully obtained peptide-specific CTL clones which also recognize and kill the tumor cells expressing the antigen.

Specifically, transfection of colon cancer HCT116 and RKO cells with small-interfering RNA (siRNA) specific to TOM34, effectively suppressed its expression, and dramatically inhibited the cell growth.

Furthermore, we examined the peptides with sequences derived from TOM34 for their potential to serve as antigenic epitope peptides and have explored a novel epitope peptide for effective cancer immunotherapy which could induce significant cellular immune response against colon cancer. Peripheral Blood Mononuclear Cells (PBMC) of healthy donors were stimulated using the peptides having partial sequences of TOM34. Those peptides were chosen that were predicted to bind to HLA-A*2402. We have successfully identified a specific antigen peptide whose sequence derived from TOM34 that could induce cytotoxic T lymphocyte (CTL) cell lines showing specific cytotoxicity against cells that present the antigen in HLA-A24-restricted manner. CTL clones were established from these CTL cell lines. Further analysis of the CTL clones showed that they had potent cytotoxic activity not only against the peptide-loaded target cells but also against the cells that endogenously express TOM34. Furthermore, cold target inhibition assay indicated that the CTL clones specifically recognized the antigen peptide in the complex of MHC Class I molecule. These results strongly suggest that the peptide is a HLA-A24-restricted epitope peptide which can induce potent and specific immune response against colon cancer cells expressing TOM34.

These findings suggest that TOM34 is involved in the growth of cancer cells, and may contribute to the development of novel anticancer drugs and/or diagnosis for CRCs.

The present invention is based on the discovery of a pattern of gene expression of TOM34. The nucleotide sequence and amino acid sequence of TOM34 are set forth in SEQ ID NO:60 and 61, respectively. These sequence are also available from Genbank Accession NO. AB085681.

Accordingly, the present invention provides a method of diagnosing or determining a predisposition to colon cancer in a subject by determining an expression level of TOM34 in a patient-derived biological sample, such as tissue sample. A normal cell is one obtained from colon tissue. An alteration, e.g., an increase in the level of expression of a gene as compared to a normal control level of the gene, indicates that the subject suffers from or is at risk of developing colon cancer.

When used in the context of the present invention the term "predisposition to colon cancer" encompasses a state of a subject of being predisposed to, having a tendency, prevalence, inclination or susceptibility to colon cancer. Moreover, said term also encompasses that a subject is at a risk of acquiring colon cancer.

In the context of the present invention, the phrase "control level" refers to a protein expression level detected in a control sample. A control level can be a single expression pattern derived from a single reference population or from a plurality of expression patterns. For example, the control level can be a database of expression patterns from previously tested cells. A "normal control level" refers to a level of gene expression detected in a normal, healthy individual or in a population of individuals known not to be suffering from colon cancer. A normal individual is one with no clinical symptoms of colon cancer.

An increase in the expression level of TOM34 detected in a test sample as compared to a normal control level indicates that the subject (from which the sample was obtained) suffers from or is at risk of developing CRC.

According to the present invention, gene expression level is deemed "altered" when gene expression is increased 10%, 25%, 50% as compared to the control level. Alternatively, an expression level is deemed "increased" when gene expression is increased by at least 0.1, at least 0.2, at least 1, at least 2, at least 5, or at least 10 or more fold as compared to a control level. Expression is determined by detecting hybridization, e.g., TOM34 probe to a gene transcript of the patient-derived tissue sample.

In the context of the present invention, the patient-derived tissue sample is any tissue obtained from a test subject, e.g., a patient known to or suspected of having colon cancer. For example, the tissue may contains an epithelial cell. More particularly, the tissue may be an epithelial cell from a colorectal carcinoma.

The present invention further provides methods of identifying an agent that inhibits the expression or activity of TOM34, by contacting a test cell expressing TOM34 with a test compound and determining the expression level of TOM34 or the activity of its gene product. The test cell may be an epithelial cell, such as an epithelial cell obtained from a colorectal carcinoma. A decrease in the expression level of TOM34 or the activity of its gene product as compared to a control level or activity of the gene or gene product indicates that the test compound is an inhibitor of TOM34 and may be used to reduce a symptom of colon cancer.

The present invention also provides a kit comprising a detection reagent which binds to TOM34 nucleic acids or polypeptides.

Therapeutic methods of the present invention include a method of treating or preventing colon cancer in a subject including the step of administering to the subject an antagonist or inhibitor of TOM34 which is, for example, an antisense composition or an antibody composition. The antagonist or inhibitor can either act on the nucleic acid or protein level so as to reduce or inhibit TOM34 expression or activity.

In the context of the present invention, the antisense composition reduces the expression of the specific target gene. For example, the antisense composition may contain a nucleotide which is complementary to TOM34 sequence. Alternatively, the present method may include the steps of administering to a subject a small interfering RNA (siRNA) composition. In the context of the present invention, the siRNA composition reduces the expression of TOM34. In yet another method, the treatment or prevention of colon cancer in a subject may be carried out by administering to a subject a ribozyme composition. In the context of the present invention, the nucleic acid-specific ribozyme composition reduces the expression of TOM34. Actually, the inhibition effect of the siRNA for TOM34 was confirmed. For example, it has been clearly shown that the siRNA for TOM34 inhibit cell proliferation of colon cancer cells in the examples section. Thus, in the present invention, TOM34 is a preferable therapeutic target of the colon cancer.

The present invention also includes vaccines and vaccination methods. For example, a method of treating or preventing colon cancer in a subject may involve administering to the subject a vaccine containing a polypeptide encoded by a nucleic acid of TOM34 or an immunologically active fragment of such a polypeptide. In the context of the present invention, an immunologically active fragment is a polypeptide that is shorter in length than the full-length naturally-occurring protein yet which induces an immune response analogous to that induced by the full-length protein. For example, an immunologically active fragment should be at least 8 residues in length and capable of stimulating an immune cell such as a T cell or a B cell. Immune cell stimulation can be measured by detecting cell proliferation, elaboration of cytokines (e.g., IL-2), or production of an antibody.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference herein in their entirety. Nothing herein is to be construed as an admission that the invention is not entitled to antedate such disclosure by virtue of prior invention.

In case of conflict, the present specification, including definitions, will control. In addition, the materials, methods, and examples are illustrative only and not intended to be limiting.

One advantage of the methods described herein is that the disease is identified prior to detection of overt clinical symptoms of colon cancer. Other features and advantages of the invention will be apparent from the following detailed description, and from the claims.

The CTL lines showed high cytotoxic activity against target cells (TISI) loaded with TOM34-299, whereas they did not show significant cytotoxic activity against the same target cells (TISI) without loaded peptide. It demonstrates that the CTL lines have the peptide-specific cytotoxicity.

Figure 6:
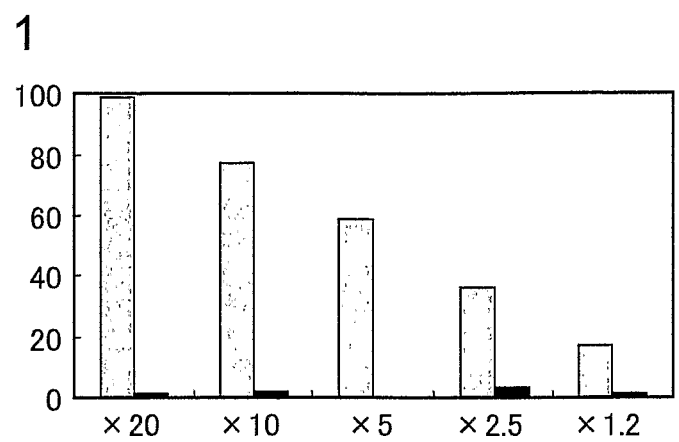
Figure 6:
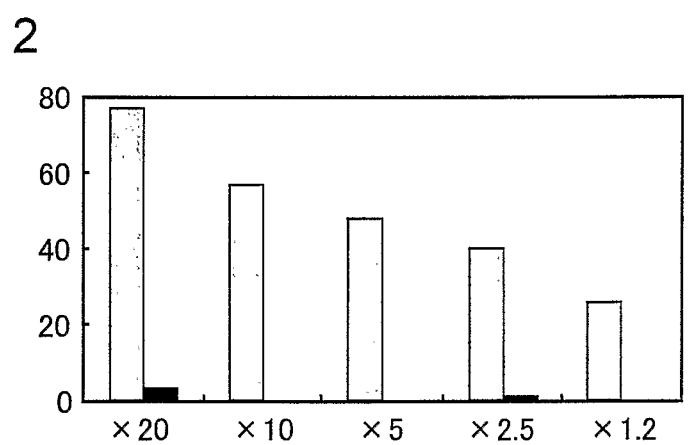

FIG. 6 depicts potent and peptide-specific cytotoxicity of the CTL lines raised by TOM34-299. (1) CLT line 1. (2) CTL line 2.

The CTL lines showed potent and antigen-specific cytotoxicity detectable at the E/T ratio of as low as 1.2.

Figure 7:
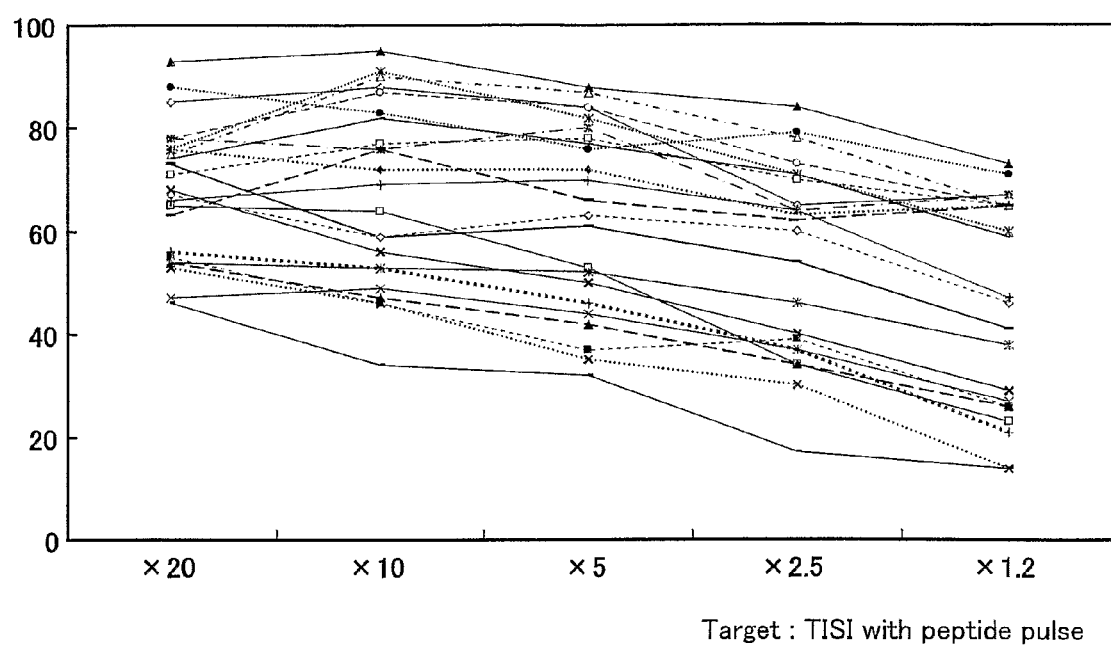

FIG. 7 depicts potent cytotoxicity of CTL clones. CTL clones with very potent cytotoxicity can be established that are specific for TOM34-299.

The CTL clones established from the CTL lines against TOM34-299 showed varied killing activities, with some of which having extremely potent activity.

Figure 8:
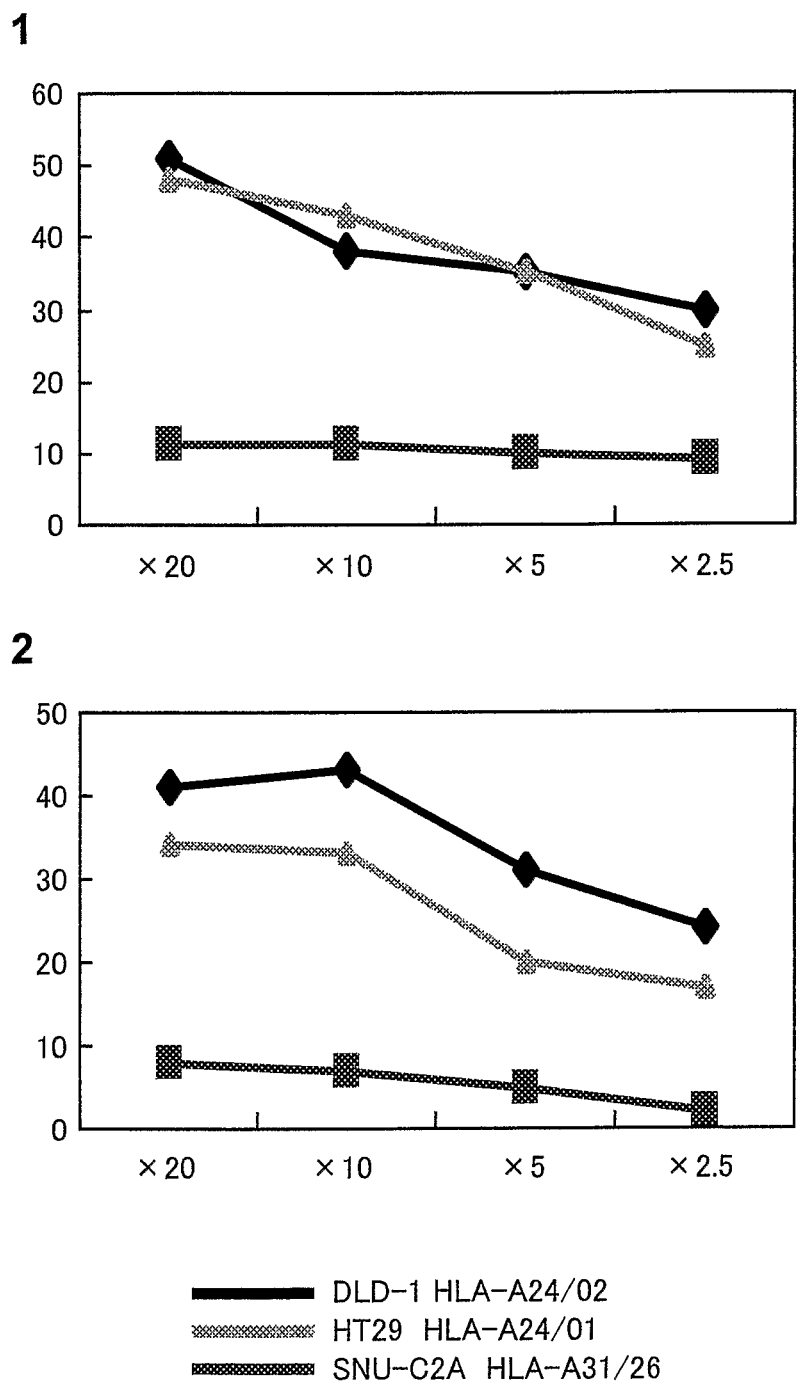

FIG. 8 depict HLA specificity of the CTL clones raised by TOM34-299. (1) CLT clone 1. (2) CTL clone 2. The CTL clones raised by TOM34-299 recognize and lyse the tumor cells endogenously expressing TOM34 in the HLA restricted fashion.

Cytotoxic activities against DLD-1 and HT29 colon cancer cell lines, which endogenously express TOM34, were tested using the two CTL clones raised by TOM34-299 as effector cells. SNU-C2A cells were used as the target which endogenously express TOM34 but do not express HLA-A24. The CTL Clones showed high cytotoxic activities against both DLD-1 and HT29 cells that express TOM34 as well as HLA-A24.

On the other hand, they showed no significant cytotoxic activity against SNU-C2A cells which express TOM34, but not HLA-A24.

Figure 9:
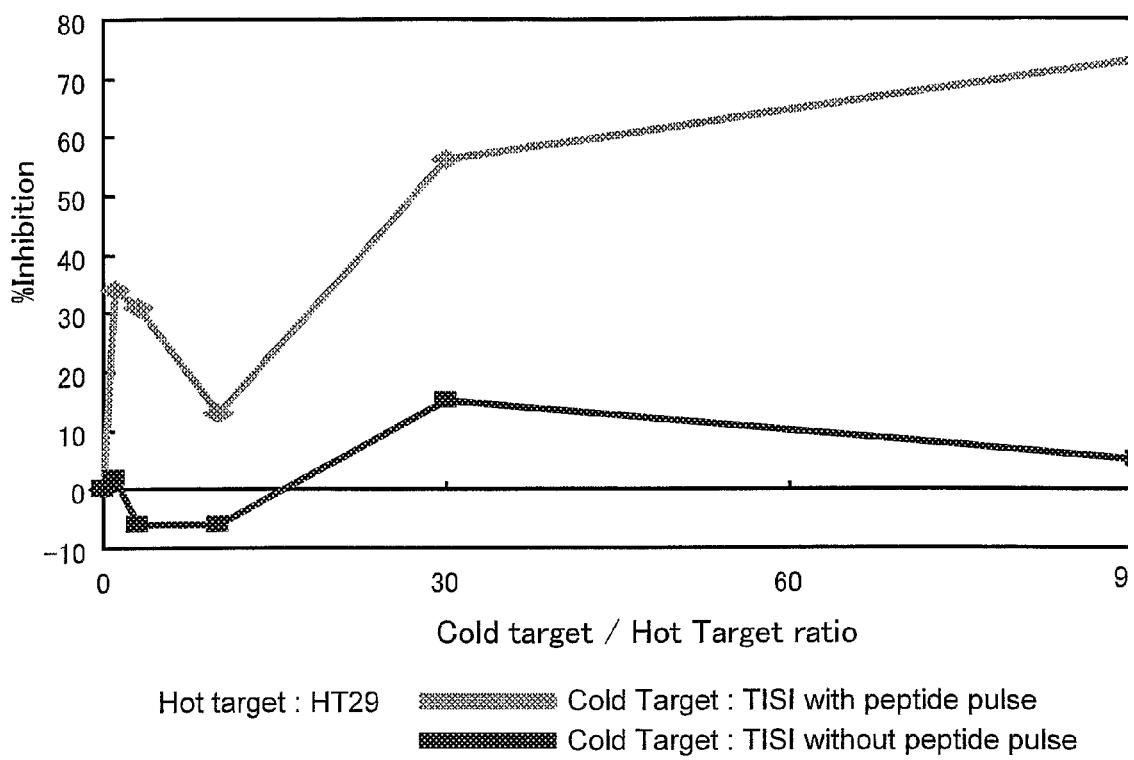

FIG. 9 depict HLA specificity of the CTL clones raised by TOM34-299. The CTL clone raised by TOM34-299 specifically recognizes TOM34 in the HLA-A24 restricted manner.

The cold target inhibition assay was performed as described in "Materials and Methods". HT29 cells labeled by $Na_2^{51}CrO_4$ were prepared as hot target, while TISI cells with or without loaded TOM34-299 peptide were used without $^{51}Cr$ labeling as cold targets. E/T ratio was fixed at 20. The cytotoxic activity of the CTL clone against HT29 cells was inhibited by the addition of TISI cells only when loaded with the peptide.

Figure 10:
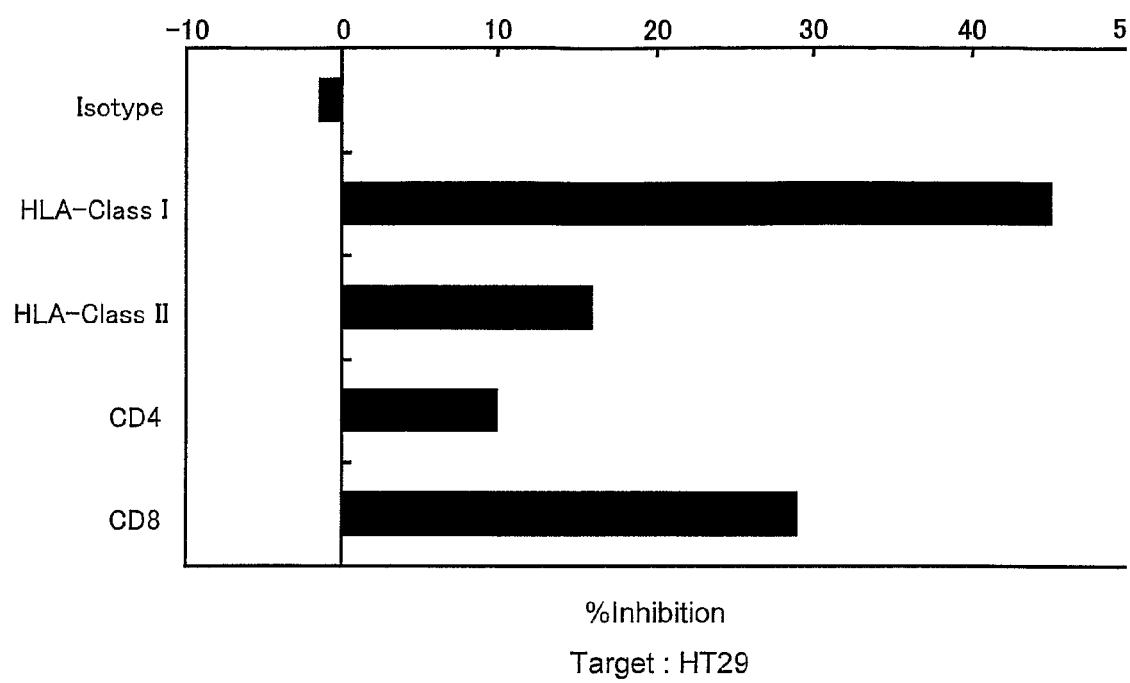

FIG. 10 depicts specificity of the cytotoxic activity of the CTL clone raised by TOM34-299. The cytotoxic activity of the CTL clone raised by TOM34-299 is specifically blocked by antibodies recognizing T cell surface antigens HLA class I or CD8.

The cytotoxic activity of the CTL clone was determined against HT29 cells in the presence of antibodies recognizing T-cell surface antigens. The CTL activity was clearly blocked by adding antibodies that recognize HLA Class I or CD8 and was marginally affected by adding antibodies to HLA Class II or CD4, while it was not inhibited at all by adding isotype-matched control antibody.

DETAILED DESCRIPTION OF THE INVENTION

The words "a", "an" and "the" as used herein mean "at least one" unless otherwise specifically indicated. Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

The present invention is based in part on the discovery of elevated expression of TOM34 in cells from colon tissues of patients with CRC. The elevated gene expression was identified by using a comprehensive cDNA microarray system.

Using a cDNA microarray containing 23,040 genes, comprehensive gene-expression profiles of 20 patients were constructed previously. TOM34 is expressed at high level in CRC patients.

TOM34 identified herein is used for diagnostic purposes as marker of CRC and as gene target, the expression of which is altered to treat or alleviate a symptom of CRC.

By measuring expression of TOM34 in a sample of cells, CRC is diagnosed. Similarly, by measuring the expression of TOM34 in response to various agents, and agents for treating CRC can be identified.

The invention involves determining (e.g., measuring) the expression of TOM34. Using sequence information provided by the GeneBank™ database entries for TOM34 sequence, TOM34 is detected and measured using techniques well known to one of ordinary skill in the art. For example, sequence within the sequence database entries corresponding to TOM34, is used to construct probes for detecting TOM34 RNA sequence in, e.g., northern blot hybridization analysis. As another example, the sequences can be used to construct primers for specifically amplifying TOM34 in, e.g, amplification-based detection methods such as reverse-transcription based polymerase chain reaction.

Expression level of TOM34 in the test cell population, e.g., a patient derived tissues sample is then compared to expression level of the TOM34 in a reference population. The reference cell population includes one or more cells for which the compared parameter is known, i.e., CRC cells or non-CRC cells.

Whether or not a pattern of gene expression in the test cell population compared to the reference cell population indicates CRC or a predisposition thereto depends upon the composition of the reference cell population. For example, if the reference cell population is composed of non-CRC cells, a similar gene expression pattern in the test cell population and reference cell population indicates the test cell population is non-CRC. Conversely, if the reference cell population is made up of CRC cells, a similar gene expression profile between the test cell population and the reference cell population indicates that the test cell population includes CRC cells.

A level of expression of TOM34 in a test cell population is considered altered in levels of expression if its expression level varies from the reference cell population by more than 1.0, 1.5, 2.0, 5.0, 10.0 or more fold from the expression level of the corresponding TOM34 in the reference cell population.

Differential gene expression between a test cell population and a reference cell population is normalized to a control nucleic acid, e.g. a housekeeping gene. For example, a control nucleic acid is one which is known not to differ depending on the canerous or non-canerous state of the cell. Expression levels of the control nucleic acid in the test and reference nucleic acid can be used to normalize signal levels in the compared populations. Control genes include β-actin, glyceraldehyde 3-phosphate dehydrogenase or ribosomal protein P1.

The test cell population is compared to multiple reference cell populations. Each of the multiple reference populations may differ in the known parameter. Thus, a test cell population may be compared to a second reference cell population known to contain, e.g., CRC cells, as well as a second reference population known to contain, e.g., non-CRC cells (normal cells). The test cell is included in a tissue type or cell sample from a subject known to contain, or to be suspected of containing, CRC cells.

The test cell is obtained from a bodily tissue or a bodily fluid, e.g., biological fluid (such as blood or urine). For example, the test cell is purified from a tissue. Preferably, the test cell population comprises an epithelial cell. The epithelial cell is from tissue known to be or suspected to be a CRC.

Cells in the reference cell population are derived from a tissue type as similar to test cell. Optionally, the reference cell population is a cell line, e.g. a CRC cell line (positive control) or a normal non-CRC cell line (negative control). Alternatively, the control cell population is derived from a database of molecular information derived from cells for which the assayed parameter or condition is known.

The subject is preferably a mammal. The mammal can be, e.g., a human, non-human primate, mouse, rat, dog, cat, horse, or cow.

Expression of TOM34 disclosed herein is determined at the protein or nucleic acid level using methods known in the art. For example, Northern hybridization analysis using probes which specifically recognize the sequence can be used to determine gene expression. Alternatively, expression is measured using reverse-transcription-based PCR assays, e.g., using primers specific for TOM34. Expression is also determined at the protein level, i.e., by measuring the levels of polypeptide encoded by the gene product described herein, or biological activity thereof. Such methods are well known in the art and include, e.g., immunoassays based on antibodies to protein encoded by TOM34. The biological activity of the protein encoded by the gene is also well known.

Diagnosing CRC:

In the context of the present invention, CRC is diagnosed by measuring the expression level of TOM34 from a test population of cells, (i.e., a patient-derived biological sample). Preferably, the test cell population contains an epithelial cell, e.g., a cell obtained from colon tissue. Gene expression can also be measured from blood or other bodily fluids such as urine. Other biological samples can be used for measuring protein levels. For example, the protein level in blood or serum derived from a subject to be diagnosed can be measured by immunoassay or other conventional biological assay.

Expression of TOM34 is determined in the test cell or biological sample and compared to the normal control expression level associated with TOM34 assayed. A normal control level is an expression profile of TOM34 typically found in a population known not to be suffering from CRC. An alteration (e.g., an increase) in the level of expression in the patient-derived tissue sample of TOM34 indicates that the subject is suffering from or is at risk of developing CRC. For example, an increase in the expression of TOM34 in the test population as compared to the normal control level indicates that the subject is suffering from or is at risk of developing CRC.

Alteration of TOM34 in the test population as compared to the normal control level indicates that the subject suffers from or is at risk of developing CRC.

The expression level of TOM34 in a biological sample can be estimated by quantifying mRNA corresponding to or protein encoded by TOM34. Quantification methods for mRNA are known to those skilled in the art. For example, the levels of TOM34 mRNA can be estimated by Northern blotting or RT-PCR. Since the nucleotide sequences of TOM34 are known, anyone skilled in the art can design the nucleotide sequences for probes or primers to quantify TOM34. For example TOM34 specific primer set comprising the nucleotide sequence of SEQ ID NOs: 43 and 44 is preferable primer.

Also the expression level of the TOM34 can be analyzed based on the activity or quantity of TOM34 protein. A method for determining the quantity of the TOM34 protein is shown in below. For example, immunoassay methods are useful for the determination of the proteins in biological materials. Any biological materials can be used as the biological sample for the determination of the protein or it's activity so long as the TOM34 gene is expressed in the sample of a colon cancer patient. For example, colon tissue sample can be mentioned as such biological sample. However, bodily fluids such as blood and urine may be also analyzed. On the other hand, a suitable method can be selected for the determination of the activity of a protein encoded by TOM34 gene according to the activity of a protein to be analyzed.

Expression level of TOM34 gene in a biological sample are estimated and compared with those in a normal sample (e.g., a sample derived from a non-diseased subject). When such a comparison shows that the expression level of the genes is higher than that in the normal sample, the subject is judged to be affected with colon cancer. The expression level of TOM34 gene in the biological samples from a normal subject and subject to be diagnosed may be determined at the same time. Alternatively, normal ranges of the expression levels can be determined by a statistical method based on the results obtained by analyzing the expression level of the gene in samples previously collected from a control group. A result obtained by comparing the sample of a subject is compared with the normal range; when the result does not fall within the normal range, the subject is judged to be affected with or is at risk of developing colon cancer.

In the present invention, a diagnostic agent for diagnosing colon cancer, is also provided. The diagnostic agent of the present invention comprises a compound that binds to a polynucleotide or a polypeptide of TOM34 gene. Preferably, an oligonucleotide that hybridizes to the polynucleotide of TOM34 gene or an antibody that binds to the polypeptide encoded by TOM34 gene may be used as such a compound. Moreover, also an aptamer, such as a RNA, DNA or peptide aptamer may be used as such a compound. Preferably, the diagnostic agent comprises a detectable label such as a fluorescent, luminescent or bioluminescent label which is commonly known in the art.

The present method of diagnosing colon cancer may be applied for assessing the efficacy of treatment of colon cancer in a subject. According to the method, a biological sample, such as a test cell population, is obtained from a subject undergoing treatment for colon cancer. The method for assessment can be conducted according to conventional methods of diagnosing colon cancer.

If desired, biological samples are obtained from the subject at various time points before, during or after the treatment. The expression level of TOM34 gene, in the biological sample is then determined and compared to a control level derived, for example, from a reference cell population which includes cells whose state of colon cancer (i.e., cancerous cell or non-cancerous cell) is known. The control level is determined in a biological sample that has not been exposed to the treatment.

If the control level is derived from a biological sample which contains no cancerous cell, a similarity between the expression level in the subject-derived biological sample and the control level indicates that the treatment is efficacious. A difference between the expression level of the TOM34 gene in the subject-derived biological sample and the control level indicates a less favorable clinical outcome or prognosis.

Identifying Agents that Inhibit TOM34 Expression:

An agent that inhibits the expression of TOM34 or the activity of its gene product can be identified by contacting a test cell population expressing TOM34 with a test agent and then determining the expression level of TOM34 or the activity of its gene product. A decrease in the level of expression of TOM34 or in the level of activity of its gene product in the presence of the agent as compared to the expression or activity level in the absence of the test agent indicates that the agent is an inhibitor of TOM34 and useful in inhibiting CRC.

The test cell population may be any cell expressing TOM34. For example, the test cell population may contain an epithelial cell, such as a cell derived from colon tissue. Furthermore, the test cell may be an immortalized cell line derived from an carcinoma cell or colorectal cancer. Alternatively, the test cell may be a cell which has been transfected with TOM34 or which has been transfected with a regulatory sequence (e.g. promoter sequence) from TOM34 operably linked to a reporter gene.

Assessing Efficacy of Treatment of CRC in a Subject:

The differentially expressed TOM34 identified herein also allow for the course of treatment of CRC to be monitored. In this method, a test cell population is provided from a subject undergoing treatment for CRC. If desired, test cell populations are obtained from the subject at various time points, before, during, and/or after treatment. Expression of TOM34 in the cell population is then determined and compared to a reference cell population which includes cells whose CRC state is known. In the context of the present invention, the reference cells should have not been exposed to the treatment of interest.

If the reference cell population contains no CRC cells, a similarity in the expression of TOM34 in the test cell population and the reference cell population indicates that the treatment of interest is efficacious. However, a difference in the expression of TOM34 in the test population and a normal control reference cell population indicates a less favorable clinical outcome or prognosis. Similarly, if the reference cell population contains CRC cells, a difference between the expression of TOM34 in the test cell population and the reference cell population indicates that the treatment of interest is efficacious, while a similarity in the expression of TOM34 in the test population and a cancer control reference cell population indicates a less favorable clinical outcome or prognosis.

Additionally, the expression level of TOM34 determined in a subject-derived biological sample obtained after treatment (i.e., post-treatment levels) can be compared to the expression level of TOM34 determined in a subject-derived biological sample obtained prior to treatment onset (i.e., pre-treatment levels). A decrease in the expression level of TOM34 in a post-treatment sample indicates that the treatment of interest is efficacious while an increase or maintenance in the expression level in the post-treatment sample indicates a less favorable clinical outcome or prognosis.

As used herein, the term "efficacious" indicates that the treatment leads to a reduction in the expression of a pathologically up-regulated gene, or a decrease in size, prevalence, or metastatic potential of CRC in a subject. When a treatment of interest is applied prophylactically, the term "efficacious" means that the treatment retards or prevents a CRC from forming or retards, prevents, or alleviates a symptom of clinical CRC. Assessment of colon tumors can be made using standard clinical protocols.

In addition, efficaciousness can be determined in association with any known method for diagnosing or treating CRC. CRC can be diagnosed, for example, by identifying symptomatic anomalies, e.g., weight loss, abdominal pain, back pain, anorexia, nausea, vomiting and generalized malaise, weakness, and jaundice.

Selecting a Therapeutic Agent for Treating CRC that is Appropriate for a Particular Individual:

Differences in the genetic makeup of individuals can result in differences in their relative abilities to metabolize various drugs. An agent that is metabolized in a subject to act as an anti-CRC agent can manifest itself by inducing a change in a gene expression pattern in the subject's cells from that characteristic of a cancerous state to a gene expression pattern characteristic of a non-cancerous state. Accordingly, the differentially expressed TOM34 disclosed herein allow for a putative therapeutic or prophylactic inhibitor of CRC to be tested in a test cell population from a selected subject in order to determine if the agent is a suitable inhibitor of CRC in the subject.

To identify an inhibitor of CRC that is appropriate for a specific subject, a test cell population from the subject is exposed to a therapeutic agent, and the expression of TOM34 is determined.

In the context of the method of the present invention, the test cell population contains a CRC cell expressing TOM34. Preferably, the test cell is an epithelial cell. For example, a test cell population may be incubated in the presence of a candidate agent and the pattern of gene expression of the test cell population may be measured and compared to one or more reference profiles, e.g., a CRC reference expression profile or a non-CRC reference expression profile.

A decrease in expression of TOM34 in a test cell population relative to a reference cell population containing CRC indicates that the agent has therapeutic potential.

In the context of the present invention, the test agent can be any compound or composition. Exemplary test agents include, but are not limited to, immunomodulatory agents.

Screening Assays for Identifying Therapeutic Agents:

Using the TOM34 gene, proteins encoded by the gene or transcriptional regulatory region of the gene, compounds can be screened that alter the expression of the gene or the biological activity of a polypeptide encoded by the gene. Such compounds are used as pharmaceuticals for treating or preventing CRC.

Therefore, the present invention provides a method of screening for a compound for treating or preventing CRC using the TOM34 polypeptide. An embodiment of this screening method comprises the steps of:

a) contacting a test compound with a polypeptide encoded by a polynucleotide of TOM34;
b) detecting the binding activity between the polypeptide and the test compound; and
c) selecting the test compound that binds to the polypeptide.

The TOM34 polypeptide to be used for screening may be a recombinant polypeptide or a protein derived from the nature or a partial peptide thereof. The polypeptide to be contacted with a test compound can be, for example, a purified polypeptide, a soluble protein, a form bound to a carrier or a fusion protein fused with other polypeptides.

As a method of screening for proteins, for example, that bind to the TOM34 polypeptide using the TOM34 polypeptide, many methods well known by a person skilled in the art can be used. Such a screening can be conducted by, for example, immunoprecipitation method, specifically, in the following manner. The gene encoding the TOM34 polypeptide is expressed in host (e.g., animal) cells and so on by inserting the gene to an expression vector for foreign genes, such as pSV2neo, pcDNA I, pcDNA3.1, pCAGGS and pCD8. The promoter to be used for the expression may be any promoter that can be used commonly and include, for example, the SV40 early promoter (Rigby in Williamson (ed.), Genetic Engineering, vol. 3. Academic Press, London, 83-141 (1981)), the EF-α promoter (Kim D W, et al., Gene 91: 217-23 (1990)), the CAG promoter (Niwa et al., Gene 108: 193-9 (1991)), the RSV LTR promoter (Cullen, Methods in Enzymology 152: 684-704 (1987)) the SRα promoter (Takebe et al., Mol Cell Biol 8: 466-72 (1988)), the CMV immediate early promoter (Seed and Aruffo, Proc Natl Acad Sci USA 84: 3365-9 (1987)), the SV40 late promoter (Gheysen and Fiers, J Mol Appl Genet. 1: 385-94 (1982)), the Adenovirus late promoter (Kaufman et al., Mol Cell Biol 9: 946-58 (1989)), the HSV TK promoter and so on. The introduction of the gene into host cells to express a foreign gene can be performed according to any methods, for example, the electroporation method (Chu et al., Nucleic Acids Res 15: 1311-26 (1987)), the calcium phosphate method (Chen and Okayama, Mol Cell Biol 7: 2745-52 (1987)), the DEAE dextran method (Lopata et al., Nucleic Acids Res 12: 5707-17 (1984); Sussman and Milman, Mol Cell Biol 4: 1641-3 (1984)), the Lipofectin method (Derijard, B Cell 76: 1025-37 (1994); Lamb et al., Nature Genetics 5: 22-30 (1993): Rabindran et al., Science 259: 230-4 (1993)) and so on. The polypeptide encoded by TOM34 gene can be expressed as a fusion protein comprising a recognition site (epitope) of a monoclonal antibody by introducing the epitope of the monoclonal antibody, whose specificity has been revealed, to the N- or C-terminus of the polypeptide. A commercially available epitope-antibody system can be used (Experimental Medicine 13: 85-90 (1995)). Vectors which can express a fusion protein with, for example, β-galactosidase, maltose binding protein, glutathione S-transferase, green florescence protein (GFP) and so on by the use of its multiple cloning sites are commercially available.

A fusion protein prepared by introducing only small epitopes consisting of several to a dozen amino acids so as not to change the property of the TOM34 polypeptide by the fusion is also reported. Epitopes, such as polyhistidine (Histag), influenza aggregate HA, human c-myc, FLAG, Vesicular stomatitis virus glycoprotein (VSV-GP), T7 gene 10 protein (T7-tag), human simple herpes virus glycoprotein (HSV-tag), E-tag (an epitope on monoclonal phage) and such, and monoclonal antibodies recognizing them can be used as the epitope-antibody system for screening proteins binding to the TOM34 polypeptide (Experimental Medicine 13: 85-90 (1995)).

In immunoprecipitation, an immune complex is formed by adding these antibodies to cell lysate prepared using an appropriate detergent. The immune complex consists of the TOM34 polypeptide, a polypeptide comprising the binding ability with the polypeptide, and an antibody. Immunoprecipitation can be also conducted using antibodies against the TOM34 polypeptide, besides using antibodies against the above epitopes, which antibodies can be prepared as described above.

An immune complex can be precipitated, for example by Protein A sepharose or Protein G sepharose when the antibody is a mouse IgG antibody. If the polypeptide encoded by TOM34 gene is prepared as a fusion protein with an epitope, such as GST, an immune complex can be formed in the same manner as in the use of the antibody against the TOM34 polypeptide, using a substance specifically binding to these epitopes, such as glutathione-Sepharose 4B.

Immunoprecipitation can be performed by following or according to, for example, the methods in the literature (Harlow and Lane, Antibodies, 511-52, Cold Spring Harbor Laboratory publications, New York (1988)).

SDS-PAGE is commonly used for analysis of immunoprecipitated proteins and the bound protein can be analyzed by the molecular weight of the protein using gels with an appropriate concentration. Since the protein bound to the TOM34 polypeptide is difficult to detect by a common staining method, such as Coomassie staining or silver staining, the detection sensitivity for the protein can be improved by culturing cells in culture medium containing radioactive isotope, $^{35}$S-methionine or $^{35}$S-cystein, labeling proteins in the cells, and detecting the proteins. The target protein can be purified directly from the SDS-polyacrylamide gel and its sequence can be determined, when the molecular weight of a protein has been revealed.

As a method for screening proteins binding to the TOM34 polypeptide using the polypeptide, for example, West-Western blotting analysis (Skolnik et al., Cell 65: 83-90 (1991)) can be used. Specifically, a protein binding to the TOM34 polypeptide can be obtained by preparing a cDNA library from cells, tissues, organs (for example, tissues such as testis or ovary), or cultured cells (e.g., CW2, DLD1, HCT116, HCT15, RKO, LS174T) expected to express a protein binding to the TOM34 polypeptide using a phage vector (e.g., ZAP), expressing the protein on LB-agarose, fixing the protein expressed on a filter, reacting the purified and labeled TOM34 polypeptide with the above filter, and detecting the plaques expressing proteins bound to the TOM34 polypeptide according to the label. The polypeptide of the invention may be labeled by utilizing the binding between biotin and avidin, or by utilizing an antibody that specifically binds to the TOM34 polypeptide, or a peptide or polypeptide (for example, GST) that is fused to the TOM34 polypeptide. Methods using radioisotope or fluorescence and such may be also used.

Alternatively, in another embodiment of the screening method of the present invention, a two-hybrid system utilizing cells may be used ("MATCHMAKER Two-Hybrid system", "MATCHMAKER Mammalian Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet 10: 286-92 (1994)").

In the two-hybrid system, the polypeptide of the invention is fused to the SRF-binding region or GAL4-binding region and expressed in yeast cells. A cDNA library is prepared from cells expected to express a protein binding to the polypeptide of the invention, such that the library, when expressed, is fused to the VP16 or GAL4 transcriptional activation region. The cDNA library is then introduced into the above yeast cells and the cDNA derived from the library is isolated from the positive clones detected (when a protein binding to the polypeptide of the invention is expressed in yeast cells, the binding of the two activates a reporter gene, making positive clones detectable). A protein encoded by the cDNA can be prepared by introducing the cDNA isolated above to E. coli and expressing the protein.

As a reporter gene, for example, Ade2 gene, lacZ gene, CAT gene, luciferase gene and such can be used in addition to the HIS3 gene.

A compound binding to the polypeptide encoded by TOM34 gene can also be screened using affinity chromatography. For example, the polypeptide of the invention may be immobilized on a carrier of an affinity column, and a test compound, containing a protein capable of binding to the polypeptide of the invention, is applied to the column. A test compound herein may be, for example, cell extracts, cell lysates, etc. After loading the test compound, the column is washed, and compounds bound to the polypeptide of the invention can be prepared.

When the test compound is a protein, the amino acid sequence of the obtained protein is analyzed, an oligo DNA is synthesized based on the sequence, and cDNA libraries are screened using the oligo DNA as a probe to obtain a DNA encoding the protein.

A biosensor using the surface plasmon resonance phenomenon may be used as a mean for detecting or quantifying the bound compound in the present invention. When such a biosensor is used, the interaction between the polypeptide of the invention and a test compound can be observed real-time as a surface plasmon resonance signal, using only a minute amount of polypeptide and without labeling (for example, BIAcore, Pharmacia). Therefore, it is possible to evaluate the binding between the polypeptide of the invention and a test compound using a biosensor such as BIAcore.

The methods of screening for molecules that bind when the immobilized TOM34 polypeptide is exposed to synthetic chemical compounds, or natural substance banks or a random phage peptide display library, and the methods of screening using high-throughput based on combinatorial chemistry techniques (Wrighton et al., Science 273: 458-64 (1996); Verdine, Nature 384: 11-13 (1996); Hogan, Nature 384: 17-9 (1996)) to isolate not only proteins but chemical compounds that bind to the TOM34 protein (including agonist and antagonist) are well known to one skilled in the art.

Alternatively, the present invention provides a method of screening for a compound for treating or preventing CRC using the polypeptide encoded by TOM34 gene comprising the steps as follows:
  a) contacting a test compound with a polypeptide encoded by a polynucleotide of TOM34;
  b) detecting the biological activity of the polypeptide of step (a); and
  c) selecting the test compound that suppresses the biological activity of the polypeptide encoded by the polynucleotide of TOM34 as compared to the biological activity of said polypeptide detected in the absence of the test compound.

Since the TOM34 protein have the activity of promoting cell proliferation of CRC cells, a compound which inhibits this activity of this protein can be screened using this activity as an index.

Any polypeptides can be used for screening so long as they comprise the biological activity of the TOM34 protein. Such biological activity include cell-proliferating activity of the human TOM34 protein. For example, a human TOM34 protein can be used and polypeptides functionally equivalent to these proteins can also be used. Such polypeptides may be expressed endogenously or exogenously by cells.

The compound isolated by this screening is a candidate for agonists or antagonists of the polypeptide encoded by TOM34 gene. The term "agonist" refers to molecules that activate the function of the polypeptide by binding thereto. Likewise, the term "antagonist" refers to molecules that inhibit the function of the polypeptide by binding thereto. Moreover, a compound isolated by this screening is a candidate for compounds which inhibit the in vivo interaction of the TOM34 polypeptide with molecules (including DNAs and proteins).

When the biological activity to be detected in the present method is cell proliferation, it can be detected, for example, by preparing cells which express the TOM34 polypeptide, culturing the cells in the presence of a test compound, and determining the speed of cell proliferation, measuring the cell cycle and such, as well as by measuring the colony forming activity as described in the Examples.

In a further embodiment, the present invention provides methods for screening compounds for treating or preventing CRC. As discussed in detail above, by controlling the expression levels of the TOM34, one can control the onset and progression of CRC. Thus, compounds that may be used in the treatment or prevention of CRC can be identified through screenings that use the expression levels of TOM34 as indices. In the context of the present invention, such screening may comprise, for example, the following steps:
 a) contacting a candidate compound with a cell expressing TOM34; and
 b) selecting the candidate compound that reduces the expression level of TOM34 as compared to a control level in the absence of the candidate compound.

Cells expressing the TOM34 include, for example, cell lines established from CRC; such cells can be used for the above screening of the present invention (e.g., CW2, DLD1, HCT116, RKO, LS174T). The expression level can be estimated by methods well known to one skilled in the art. In the method of screening, a compound that reduces the expression level of TOM34 can be selected as candidate agents to be used for the treatment or prevention of CRC.

Alternatively, the screening method of the present invention may comprise the following steps:
 a) contacting a candidate compound with a cell into which a vector, comprising the transcriptional regulatory region of TOM34 and a reporter gene that is expressed under the control of the transcriptional regulatory region, has been introduced;
 b) measuring the expression or activity of said reporter gene; and
 c) selecting the candidate compound that reduces the expression or activity of said reporter gene.

Suitable reporter genes and host cells are well known in the art. The reporter construct required for the screening can be prepared by using the transcriptional regulatory region of a marker gene. When the transcriptional regulatory region of a marker gene has been known to those skilled in the art, a reporter construct can be prepared by using the previous sequence information. When the transcriptional regulatory region of a marker gene remains unidentified, a nucleotide segment containing the transcriptional regulatory region can be isolated from a genome library based on the nucleotide sequence information of the marker gene.

Examples of supports that may be used for binding proteins include insoluble polysaccharides, such as agarose, cellulose and dextran; and synthetic resins, such as polyacrylamide, polystyrene and silicon; preferably commercial available beads and plates (e.g., multi-well plates, biosensor chip, etc.) prepared from the above materials may be used. When using beads, they may be filled into a column.

The binding of a protein to a support may be conducted according to routine methods, such as chemical bonding and physical adsorption. Alternatively, a protein may be bound to a support via antibodies specifically recognizing the protein. Moreover, binding of a protein to a support can be also conducted by means of avidin and biotin.

The binding between proteins is carried out in buffer, for example, but are not limited to, phosphate buffer and Tris buffer, as long as the buffer does not inhibit the binding between the proteins.

In the present invention, a biosensor using the surface plasmon resonance phenomenon may be used as a mean for detecting or quantifying the bound protein. When such a biosensor is used, the interaction between the proteins can be observed real-time as a surface plasmon resonance signal, using only a minute amount of polypeptide and without labeling (for example, BIAcore, Pharmacia).

Alternatively, TOM34 polypeptide may be labeled, and the label of the bound protein may be used to detect or measure the bound protein. Specifically, after pre-labeling one of the proteins, the labeled protein is contacted with the other protein in the presence of a test compound, and then bound proteins are detected or measured according to the label after washing.

Labeling substances such as radioisotope (e.g., $^3$H, $^{14}$C, $^{32}$P, $^{33}$P, $^{35}$S, $^{125}$I, $^{131}$I), enzymes (e.g., alkaline phosphatase, horseradish peroxidase, β-galactosidase, β-glucosidase), fluorescent substances (e.g., fluorescein isothiosyanete (FITC), rhodamine) and biotin/avidin, may be used for the labeling of a protein in the present method. When the protein is labeled with radioisotope, the detection or measurement can be carried out by liquid scintillation. Alternatively, proteins labeled with enzymes can be detected or measured by adding a substrate of the enzyme to detect the enzymatic change of the substrate, such as generation of color, with absorptiometer. Further, in case where a fluorescent substance is used as the label, the bound protein may be detected or measured using fluorophotometer.

In case of using an antibody in the present screening, the antibody is preferably labeled with one of the labeling substances mentioned above, and detected or measured based on the labeling substance. Alternatively, the antibody against the TOM34 polypeptide or actin may be used as a primary antibody to be detected with a secondary antibody that is labeled with a labeling substance. Furthermore, the antibody bound to the protein in the screening of the present invention may be detected or measured using protein G or protein A column.

Alternatively, in another embodiment of the screening method of the present invention, a two-hybrid system utilizing cells may be used ("MATCHMAKER Two-Hybrid system", "MATCHMAKER Mammalian Two-Hybrid Assay Kit", "MATCHMAKER one-Hybrid system" (Clontech); "HybriZAP Two-Hybrid Vector System" (Stratagene); the references "Dalton and Treisman, Cell 68: 597-612 (1992)", "Fields and Sternglanz, Trends Genet 10: 286-92 (1994)").

In the two-hybrid system, the TOM34 polypeptide of the invention is fused to the SRF-binding region or GAL4-binding region and expressed in yeast cells.

As a reporter gene, for example, Ade2 gene, lacZ gene, CAT gene, luciferase gene and such can be used besides HIS3 gene.

Any test compound, for example, cell extracts, cell culture supernatant, products of fermenting microorganism, extracts from marine organism, plant extracts, purified or crude proteins, peptides, non-peptide compounds, synthetic micromolecular compounds and natural compounds can be used in the screening methods of the present invention. In the present invention, the test compound can be also obtained using any of the numerous approaches in combinatorial library methods known in the art, including (1) biological libraries, (2) spatially addressable parallel solid phase or solution phase libraries, (3) synthetic library methods requiring deconvolution, (4) the "one-bead one-compound" library method and (5) synthetic library methods using affinity chromatography selection. The biological library methods using affinity chromatography selection is limited to peptide libraries, while the other four approaches are applicable to peptide, non-peptide oligomer or small molecule libraries of compounds (Lam (1997) Anticancer Drug Des. 12: 145-67). Examples of methods for the synthesis of molecular libraries can be found in the art (DeWitt et al. (1993) Proc. Natl. Acad. Sci. USA 90: 6909-13; Erb et al. (1994) Proc. Natl. Acad. Sci. USA 91:

11422-6; Zuckermann et al. (1994) J. Med. Chem. 37: 2678-85; Cho et al. (1993) Science 261: 1303-5; Carell et al. (1994) Angew. Chem. Int. Ed. Engl. 33: 2059; Carell et al. (1994) Angew. Chem. Int. Ed. Engl. 33: 2061; Gallop et al. (1994) J. Med. Chem. 37: 1233-51). Libraries of compounds may be presented in solution (see Houghten (1992) Bio/Techniques 13: 412-21) or on beads (Lam (1991) Nature 354: 82-4), chips (Fodor (1993) Nature 364: 555-6), bacteria (U.S. Pat. No. 5,223,409), spores (U.S. Pat. Nos. 5,571,698; 5,403,484, and 5,223,409), plasmids (Cull et al. (1992) Proc. Natl. Acad. Sci. USA 89: 1865-9) or phage (Scott and Smith (1990) Science 249: 386-90; Devlin (1990) Science 249: 404-6; Cwirla et al. (1990) Proc. Natl. Acad. Sci. USA 87: 6378-82; Felici (1991) J. Mol. Biol. 222: 301-10; US Pat. Application 2002103360).

A compound isolated by the screening methods of the present invention is a candidate for drugs which inhibit the activity of the TOM34 polypeptide, for treating or preventing diseases attributed to, for example, cell proliferative diseases, such as CRC. A compound in which a part of the structure of the compound obtained by the present screening methods of the present invention is converted by addition, deletion and/or replacement, is included in the compounds obtained by the screening methods of the present invention.

Pharmaceutical Compositions for Treating or Preventing CRC

When administrating a compound isolated by the method of the present invention as a pharmaceutical for humans and other mammals, such as mice, rats, guinea-pigs, rabbits, cats, dogs, sheep, pigs, cattle, monkeys, baboons, and chimpanzees, the isolated compound can be directly administered or can be formulated into a dosage form using known pharmaceutical preparation methods. For example, according to the need, the drugs can be taken orally, as sugar-coated tablets, capsules, elixirs and microcapsules, or non-orally, in the form of injections of sterile solutions or suspensions with water or any other pharmaceutically acceptable liquid. For example, the compounds can be mixed with pharmaceutically acceptable carriers or media, specifically, sterilized water, physiological saline, plant-oils, emulsifiers, suspending agents, surfactants, stabilizers, flavoring agents, excipients, vehicles, preservatives, binders, and such, in a unit dose form required for generally accepted drug implementation. The amount of active ingredient contained in such a preparation makes a suitable dosage within the indicated range acquirable.

Examples of additives that can be admixed into tablets and capsules include, but are not limited to, binders, such as gelatin, corn starch, tragacanth gum and arabic gum; excipients, such as crystalline cellulose; swelling agents, such as corn starch, gelatin and alginic acid; lubricants, such as magnesium stearate; sweeteners, such as sucrose, lactose or saccharin; and flavoring agents, such as peppermint, Gaultheria adenothrix oil and cherry. When the unit-dose form is a capsule, a liquid carrier, such as an oil, can be further included in the above ingredients. Sterile composites for injection can be formulated following normal drug implementations using vehicles, such as distilled water, suitable for injection.

Physiological saline, glucose, and other isotonic liquids, including adjuvants, such as D-sorbitol, D-mannnose, D-mannitol, and sodium chloride, can be used as aqueous solutions for injection. These can be used in conjunction with suitable solubilizers, such as alcohol, for example, ethanol; polyalcohols, such as propylene glycol and polyethylene glycol; and non-ionic surfactants, such as Polysorbate 80™ and HCO-50.

Sesame oil or soy-bean oil can be used as an oleaginous liquid, may be used in conjunction with benzyl benzoate or benzyl alcohol as a solubilizer, and may be formulated with a buffer, such as phosphate buffer and sodium acetate buffer; a pain-killer, such as procaine hydrochloride; a stabilizer, such as benzyl alcohol and phenol; and/or an anti-oxidant. A prepared injection may be filled into a suitable ampoule.

Methods well known to those skilled in the art may be used to administer the pharmaceutical composition of the present invention to patients, for example as an intraarterial, intravenous, or percutaneous injection or as an intranasal, transbronchial, intramuscular or oral administration. The dosage and method of administration vary according to the body-weight and age of a patient and the administration method; however, one skilled in the art can routinely select a suitable method of administration. If said compound is encodable by a DNA, the DNA can be inserted into a vector for gene therapy and the vector administered to a patient to perform the therapy. The dosage and method of administration vary according to the body-weight, age, and symptoms of the patient; however, one skilled in the art can suitably select them.

For example, although the dose of a compound that binds to a protein of the present invention and regulates its activity depends on the symptoms, the dose is generally about 0.1 mg to about 100 mg per day, preferably about 1.0 mg to about 50 mg per day and more preferably about 1.0 mg to about 20 mg per day, when administered orally to a normal adult human (weight 60 kg).

When administering the compound parenterally, in the form of an injection to a normal adult human (weight 60 kg), although there are some differences according to the patient, target organ, symptoms and method of administration, it is convenient to intravenously inject a dose of about 0.01 mg to about 30 mg per day, preferably about 0.1 to about 20 mg per day and more preferably about 0.1 to about 10 mg per day. In the case of other animals, the appropriate dosage amount may be routinely calculated by converting to 60 kgs of body-weight.

Assessing the Prognosis of a Subject with CRC:

The present invention also provides a method of assessing the prognosis of a subject with CRC including the step of comparing the expression of TOM34 in a test cell population to the expression of TOM34 in a reference cell population derived from patients over a spectrum of disease stages. By comparing the gene expression of TOM34 in the test cell population and the reference cell population(s), or by comparing the pattern of gene expression over time in test cell populations derived from the subject, the prognosis of the subject can be assessed.

For example, an increase in the expression of TOM34 as compared to a normal control indicates less favorable prognosis. Conversely, a similarity in the expression of TOM34 as compared to normal control indicates a more favorable prognosis for the subject.

Kits:

The present invention also includes a CRC-detection reagent, e.g., a nucleic acid that specifically binds to or identifies TOM34 nucleic acids, such as oligonucleotide sequences which are complementary to a portion of TOM34 nucleic acid, or an antibody that bind to proteins encoded by TOM34 nucleic acid, or an aptamer. The detection reagents may be packaged together in the form of a kit. For example, the detection reagents may be packaged in separate containers, e.g., a nucleic acid or antibody (either bound to a solid matrix or packaged separately with reagents for binding them to the matrix), a control reagent (positive and/or negative), and/or a detectable label. Instructions (e.g., written, tape, VCR, CD-ROM, etc.) for carrying out the assay may also be included in the kit. The assay format of the kit may be a Northern hybridization or a sandwich ELISA, both of which are known in the art.

For example, a CRC detection reagent may be immobilized on a solid matrix, such as a porous strip, to form at least one CRC detection site. The measurement or detection region of the porous strip may include a plurality of sites, each containing a nucleic acid. A test strip may also contain sites for negative and/or positive controls. Alternatively, control sites may be located on a separate strip from the test strip. Optionally, the different detection sites may contain different amounts of immobilized nucleic acids, i.e., a higher amount in the first detection site and lesser amounts in subsequent sites. Upon the addition of test sample, the number of sites displaying a detectable signal provides a quantitative indication of the amount of CRC present in the sample. The detection sites may be configured in any suitably detectable shape and are typically in the shape of a bar or dot spanning the width of a test strip.

Methods of Inhibiting CRC:

The present invention further provides a method for treating or alleviating a symptom of CRC in a subject by decreasing the expression of TOM34 (or the activity of its gene product). Suitable therapeutic compounds can be administered prophylactically or therapeutically to a subject suffering from or at risk of (or susceptible to) developing CRC. Such subjects can be identified using standard clinical methods or by detecting an aberrant level of expression of TOM34 or aberrant activity of its gene product. In the context of the present invention, suitable therapeutic agents include, for example, inhibitors of cell cycle regulation and cell proliferation.

Alternatively, the therapeutic method of the present invention may include the step of decreasing the expression, function, or both, of gene products of TOM34 whose expression is aberrantly increased ("up-regulated" or "over-expressed" gene) in colon cells. Expression may be inhibited in any of several ways known in the art. For example, expression can be inhibited by administering to the subject a nucleic acid that inhibits, or antagonizes the expression of the over-expressed gene, e.g., an antisense oligonucleotide or small interfering RNA which disrupts expression of the over-expressed gene.

Of course, the herein described embodiments for methods of treatment or alleviation apply, mutatis mutands, to the use of a compound which decreases the expression of TOM34 (or the activity of its gene product) as described herein for the preparation of a pharmaceutical composition for treating or alleviating colon cancer in a subject. Such a compound could be, for example, an antisense, siRNA, antibody, aptamers or ribozyme composition.

Antisense Nucleic Acids and siRNA:

As noted above, antisense nucleic acids corresponding to the nucleotide sequence of TOM34 can be used to reduce the expression level of the gene. Antisense nucleic acids corresponding to TOM34 that are up-regulated in CRC are useful for the treatment of CRC. Specifically, the antisense nucleic acids of the present invention may act by binding to nucleotide sequence of TOM34, or mRNAs corresponding thereto, thereby inhibiting the transcription or translation of the genes, promoting the degradation of the mRNAs, and/or inhibiting the expression of proteins encoded by TOM34, thereby, inhibiting the function of the proteins. The term "antisense nucleic acids" as used herein encompasses both nucleotides that are entirely complementary to the target sequence and those having a mismatch of one or more nucleotides, so long as the antisense nucleic acids can specifically hybridize to the target sequences. For example, the antisense nucleic acids of the present invention include polynucleotides that have a homology of at least 70% or higher, preferably at least 80% or higher, more preferably at least 90% or higher, even more preferably at least 95% or higher over a span of at least 15 continuous nucleotides. Algorithms known in the art can be used to determine the homology.

The antisense nucleic acid of the present invention act on cells producing the proteins encoded by TOM34 by binding to the DNA or mRNA encoding the protein, inhibiting their transcription or translation, promoting the degradation of the mRNA, and inhibiting the expression of the protein, thereby resulting in the inhibition of the protein function.

An antisense nucleic acid of the present invention can be made into an external preparation, such as a liniment or a poultice, by admixing it with a suitable base material which is inactive against the nucleic acid.

Also, as needed, the antisense nucleic acids of the present invention can be formulated into tablets, powders, granules, capsules, liposome capsules, injections, solutions, nose-drops and freeze-drying agents by adding excipients, isotonic agents, solubilizers, stabilizers, preservatives, pain-killers, and such. These can be prepared by following known methods.

The antisense nucleic acids of the present invention can be given to the patient by direct application onto the ailing site or by injection into a blood vessel so that it will reach the site of ailment. An antisense-mounting medium can also be used to increase durability and membrane-permeability. Examples include, but are not limited to, liposomes, poly-L-lysine, lipids, cholesterol, lipofectine or derivatives of these.

The dosage of the antisense nucleic acid derivative of the present invention can be adjusted suitably according to the patient's condition and used in desired amounts. For example, a dose range of 0.1 to 100 mg/kg, preferably 0.1 to 50 mg/kg can be administered.

The antisense nucleic acids of the present invention inhibit the expression of a protein of the present invention and are thereby useful for suppressing the biological activity of the protein of the invention. In addition, expression-inhibitors, comprising antisense nucleic acids of the present invention, are useful in that they can inhibit the biological activity of a protein of the present invention.

Binding of the siRNA to a transcript corresponding to TOM34 in the target cell results in a reduction in the protein production by the cell. The length of the oligonucleotide is at least 10 nucleotides and may be as long as the naturally-occurring transcript. Preferably, the oligonucleotide is less than 75, 50, 25 nucleotides in length. Most preferably, the oligonucleotide is 19-25 nucleotides in length.

The antisense nucleic acids of present invention include modified oligonucleotides. For example, thioated oligonucleotides may be used to confer nuclease resistance to an oligonucleotide.

Also, an siRNA against TOM34 can be used to reduce the expression level of TOM34. Herein, term "siRNA" refers to a double stranded RNA molecule which prevents translation of a target mRNA. Standard techniques for introducing siRNA into the cell may be used, including those in which DNA is a template from which RNA is transcribed. In the context of the present invention, the siRNA comprises a sense nucleic acid sequence and an anti-sense nucleic acid sequence against an up-regulated marker gene, such as TOM34. The siRNA is constructed such that a single transcript has both the sense and complementary antisense sequences of the target gene, e.g., a hairpin.

An siRNA of TOM34 hybridizes to target mRNA and thereby decreases or inhibits production of the polypeptides encoded by TOM34 by associating with the normally single-stranded mRNA transcript, thereby interfering with translation and thus, expression of the protein. Thus, siRNA molecules of the invention can be defined by their ability to hybridize specifically to mRNA of TOM34 under stringent conditions. For the purposes of this invention the terms "hybridize" or "hybridize specifically" are used to refer the ability of two nucleic acid molecules to hybridize under "stringent hybridization conditions." The phrase "stringent hybridization conditions" refers to conditions under which a nucleic acid molecule will hybridize to its target sequence, typically in a complex mixture of nucleic acids, but not detectably to other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times of background, preferably 10 times of background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 50° C.

In the context of the present invention, an siRNA is preferably less than 500, 200, 100, 50, or 25 nucleotides in length. More preferably an siRNA is 19-25 nucleotides in length. Exemplary nucleic acid sequence for the production of TOM34 siRNA includes the sequences of nucleotides of SEQ ID NO: 48 or 52 as the target sequence. In RNA or derivatives thereof, base "t" should be replaced with "u" in the nucleotide sequences. Accordingly, for example, the present invention provides a double stranded RNA molecule comprising nucleotide sequence 5'-gaaaguguucucuacucca-3' (SEQ ID NO: 48) or 5'-ggauggaaacugcagagac-3' (SEQ ID NO: 52). In order to enhance the inhibition activity of the siRNA, nucleotide "u" can be added to 3' end of the antisense strand of the target sequence. The number of "u"s to be added is at least 2, generally 2 to 10, preferably 2 to 5. The added "u"s form single strand at the 3'end of the antisense strand of the siRNA.

An siRNA of TOM34 can be directly introduced into the cells in a form that is capable of binding to the mRNA transcripts. In these embodiments, the siRNA molecules of the invention are typically modified as described above for antisense molecules. Other modifications are also possible, for example, cholesterol-conjugated siRNAs have shown improved pharmacological properties (Song et al. Nature Med. 9:347-351 (2003)). Alternatively, a DNA encoding the siRNA may be carried in a vector.

Vectors may be produced, for example, by cloning TOM34 target sequence into an expression vector having operatively-linked regulatory sequences flanking the sequence in a manner that allows for expression (by transcription of the DNA molecule) of both strands (Lee, N. S. et al., (2002) Nature Biotechnology 20:500-505). An RNA molecule that is antisense to mRNA of TOM34 is transcribed by a first promoter (e.g., a promoter sequence 3' of the cloned DNA) and an RNA molecule that is the sense strand for the mRNA of TOM34 is transcribed by a second promoter (e.g., a promoter sequence 5' of the cloned DNA). The sense and antisense strands hybridize in vivo to generate siRNA constructs for silencing of TOM34. Alternatively, the two constructs can be utilized to create the sense and anti-sense strands of a siRNA construct. Cloned TOM34 can encode a construct having secondary structure, e.g., hairpins, wherein a single transcript has both the sense and complementary antisense sequences from the target gene.

A loop sequence consisting of an arbitrary nucleotide sequence can be located between the sense and antisense sequence in order to form the hairpin loop structure. Thus, the present invention also provides siRNA having the general formula 5'-[A]-[B]-[A']-3', wherein [A] is a ribonucleotide sequence corresponding to a sequence that specifically hybridizes to an mRNA or a cDNA of TOM34. In preferred embodiments, [A] is a ribonucleotide sequence corresponding a sequence of TOM34,

[B] is a ribonucleotide sequence consisting of 3 to 23 nucleotides, and

[A'] is a ribonucleotide sequence consisting of the complementary sequence of [A]. The region [A] hybridizes to [A'], and then a loop consisting of region [B] is formed. The loop sequence may be preferably 3 to 23 nucleotide in length. The loop sequence, for example, can be selected from group consisting of following sequences (on the world wide web at www.ambion.com/techlib/tb/tb_506.html). Furthermore, loop sequence consisting of 23 nucleotides also provides active siRNA (Jacque, J.-M., et al., (2002) Nature 418: 435-438).

CCC, CCACC or CCACACC: Jacque, J. M, et al., (2002) Nature, Vol. 418: 435-438.

UUCG: Lee, N. S., et al., (2002) Nature Biotechnology 20: 500-505. Fruscoloni, P., et al., (2003) Proc. Natl. Acad. Sci. USA 100(4): 1639-1644.

UUCAAGAGA: Dykxhoorn, D. M., et al., (2002) Nature Reviews Molecular Cell Biology 4: 457-467.

Accordingly, the loop sequence can be selected from group consisting of, CCC, UUCG, CCACC, CCACACC, and UUCAAGAGA. Preferable loop sequence is UUCAAGAGA ("ttcaagaga" in DNA). Exemplary hairpin siRNA suitable for use in the context of the present invention include:

for TOM34-siRNA-D (siD, for target sequence of SEQ ID NO: 48) 5'-gaaaguguucucuacucca-[B]-uggaguagagaacacuuuc-3' (SEQ ID NO: 63) and for TOM34-siRNA-E (siE, for target sequence of SEQ ID NO: 52) 5'-ggauggaaacugcagagac-[B]-gucucugcaguuucca-ucc-3' (SEQ ID NO: 64)

The nucleotide sequence of suitable siRNAs can be designed using an siRNA design computer program available from the Ambion website (on the world wide web at www.ambion.com/techlib/misc/siRNA_finder.html). The computer program selects nucleotide sequences for siRNA synthesis based on the following protocol.

Selection of siRNA Target Sites:

1. Beginning with the AUG start codon of the object transcript, scan downstream for AA dinucleotide sequences. Record the occurrence of each AA and the 3' adjacent 19 nucleotides as potential siRNA target sites. Tuschl, et al. don't recommend against designing siRNA to the 5' and 3' untranslated regions (UTRs) and regions near the start codon (within 75 bases) as these may be richer in regulatory protein binding sites. UTR-binding proteins and/or translation initiation complexes may interfere with binding of the siRNA endonuclease complex.

2. Compare the potential target sites to the human genome database and eliminate from consideration any target sequences with significant homology to other coding sequences. The homology search can be performed using BLAST, which can be found on the NCBI server at: worldwide-web.ncbi.nlm.nih.gov/BLAST/.
3. Select qualifying target sequences for synthesis. At Ambion, preferably several target sequences can be selected along the length of the gene to evaluate.

The regulatory sequences flanking TOM34 gene sequences can be identical or different, such that their expression can be modulated independently, or in a temporal or spatial manner. siRNAs are transcribed intracellularly by cloning TOM34 templates, respectively, into a vector containing, e.g., a RNA polymerase III transcription unit from the small nuclear RNA (snRNA) U6 or the human H1 RNA promoter. For introducing the vector into the cell, transfection-enhancing agent can be used. FuGENE (Rochediagnostices), Lipofectamine 2000 (Invitrogen), Oligofectamine (Invitrogen), and Nucleofector (Wako pure Chemical) are useful as the transfection-enhancing agent.

The antisense oligonucleotide or siRNA of the present invention inhibits the expression of a polypeptide of the present invention and is thereby useful for suppressing the biological activity of a polypeptide of the invention. Also, expression-inhibitors, comprising the antisense oligonucleotide or siRNA of the invention, are useful in the point that they can inhibit the biological activity of the polypeptide of the invention. Therefore, a composition comprising an antisense oligonucleotide or siRNA of the present invention is useful for treating a CRC.

Antibodies:

Alternatively, function of gene product of TOM34 which is over-expressed in CRC can be inhibited by administering a compound that binds to or otherwise inhibits the function of the gene products. For example, the compound is an antibody which binds to the gene product of TOM34.

The present invention refers to the use of antibodies, particularly antibodies against a protein encoded by TOM34, or a fragment of such an antibody. As used herein, the term "antibody" refers to an immunoglobulin molecule having a specific structure, that interacts (i.e., binds) only with the antigen that was used for synthesizing the antibody (i.e., the gene product of an up-regulated marker) or with an antigen closely related thereto. Furthermore, an antibody may be a fragment of an antibody or a modified antibody, so long as it binds to the protein encoded by TOM34. For instance, the antibody fragment may be Fab, F(ab')$_2$, Fv, or single chain Fv (scFv), in which Fv fragments from H and L chains are ligated by an appropriate linker (Huston J. S. et al. Proc. Natl. Acad. Sci. U.S.A. 85:5879-5883 (1988)). More specifically, an antibody fragment may be generated by treating an antibody with an enzyme, such as papain or pepsin. Alternatively, a gene encoding the antibody fragment may be constructed, inserted into an expression vector, and expressed in an appropriate host cell (see, for example, Co M. S. et al. J. Immunol. 152:2968-2976 (1994); Better M. and Horwitz A. H. Methods Enzymol. 178:476-496 (1989); Pluckthun A. and Skerra A. Methods Enzymol. 178:497-515 (1989); Lamoyi E. Methods Enzymol. 121:652-663 (1986); Rousseaux J. et al. Methods Enzymol. 121:663-669 (1986); Bird R. E. and Walker B. W. Trends Biotechnol. 9:132-137 (1991)).

An antibody may be modified by conjugation with a variety of molecules, such as polyethylene glycol (PEG). The present invention provides such modified antibodies. The modified antibody can be obtained by chemically modifying an antibody. Such modification methods are conventional in the field.

Alternatively, an antibody may comprise a chimeric antibody having a variable region derived from a nonhuman antibody and a constant region derived from a human antibody, or a humanized antibody, comprising a complementarity determining region (CDR) derived from a nonhuman antibody, a frame work region (FR) and a constant region derived from a human antibody. Such antibodies can be prepared by using known technologies. Humanization can be performed by substituting rodent CDRs or CDR sequences for the corresponding sequences of a human antibody (see e.g., Verhoeyen et al., Science 239:1534-1536 (1988)). Accordingly, such humanized antibodies are chimeric antibodies, wherein substantially less than an intact human variable domain has been substituted by the corresponding sequence from a non-human species.

Fully human antibodies comprising human variable regions in addition to human framework and constant regions can also be used. Such antibodies can be produced using various techniques known in the art. For example in vitro methods involve use of recombinant libraries of human antibody fragments displayed on bacteriophage (e.g., Hoogenboom & Winter, J. Mol. Biol. 227:381-8 (1991), Similarly, human antibodies can be made by introducing of human immunoglobulin loci into transgenic animals, e.g., mice in which the endogenous immunoglobulin genes have been partially or completely inactivated. This approach is described, e.g., in U.S. Pat. Nos. 6,150,584; 5,545,807; 5,545,806; 5,569,825; 5,625,126; 5,633,425; 5,661,016.

Cancer therapies directed at specific molecular alterations that occur in cancer cells have been validated through clinical development and regulatory approval of anti-cancer drugs such as trastuzumab (Herceptin) for the treatment of advanced breast cancer, imatinib mesylate (Gleevec) for chronic myeloid leukemia, gefitinib (Iressa) for non-small cell lung cancer (NSCLC), and rituximab (anti-CD20 mAb) for B-cell lymphoma and mantle cell lymphoma (Ciardiello F. et al., Clin Cancer Res. 2001 October; 7(10):2958-70. Slamon D J. et al., N Engl J Med. 2001 Mar. 15; 344(11):783-92; Rehwald U. et al., Blood. 2003 Jan. 15; 101(2):420-424; Fang G. et al., (2000). Blood, 96, 2246-2253). These drugs are clinically effective and better tolerated than traditional anti-cancer agents because they target only transformed cells. Hence, such drugs not only improve survival and quality of life for cancer patients, but also validate the concept of molecularly targeted cancer therapy. Furthermore, targeted drugs can enhance the efficacy of standard chemotherapy when used in combination with it (Gianni L. (2002). Oncology, 63 Suppl 1, 47-56; Klejman A. et al., (2002). Oncogene, 21, 5868-5876). Therefore, future cancer treatments will probably involve combining conventional drugs with target-specific agents aimed at different characteristics of tumor cells such as angiogenesis and invasiveness.

These modulatory methods can be performed ex vivo or in vitro (e.g., by culturing the cell with the agent) or, alternatively, in vivo (e.g., by administering the agent to a subject). The methods involve administering a protein or combination of proteins or a nucleic acid molecule or combination of nucleic acid molecules as therapy to counteract aberrant expression of the differentially expressed genes or aberrant activity of their gene products.

Diseases and disorders that are characterized by increased (relative to a subject not suffering from the disease or disorder) expression levels or biological activities of genes and gene products, respectively, may be treated with therapeutics that antagonize (i.e., reduce or inhibit) activity of the overexpressed gene or genes. Therapeutics that antagonize activity can be administered therapeutically or prophylactically.

Accordingly, therapeutics that may be utilized in the context of the present invention include, e.g., (i) a polypeptide of the over-expressed gene or analogs, derivatives, fragments or homologs thereof; (ii) antibodies to the over-expressed gene or gene products; (iii) nucleic acids encoding the over-expressed gene; (iv) antisense nucleic acids or nucleic acids that are "dysfunctional" (i.e., due to a heterologous insertion within the nucleic acids of over-expressed gene); (v) small interfering RNA (siRNA); or (vi) modulators (i.e., inhibitors, antagonists that alter the interaction between an over-expressed polypeptide and its binding partner). The dysfunctional antisense molecules are utilized to "knockout" endogenous function of a polypeptide by homologous recombination (see, e.g., Capecchi, Science 244: 1288-1292 1989).

Increased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of a gene whose expression is altered). Methods well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, etc.).

Prophylactic administration occurs prior to the manifestation of overt clinical symptoms of disease, such that a disease or disorder is prevented or, alternatively, delayed in its progression.

Therapeutic methods of the present invention may include the step of contacting a cell with an agent that modulates one or more of the activities of the gene products of the differentially expressed genes. Examples of agent that modulates protein activity include, but are not limited to, nucleic acids, proteins, naturally-occurring cognate ligands of such proteins, peptides, peptidomimetics, and other small molecule.

Vaccinating Against CRC:

In the present invention, peptide derived from TOM34 was shown to be TAA epitopes restricted by HLA-A24 which is a common HLA allele in Japanese and Caucasian populations. Candidates of HLA-A24 binding peptides derived from TOM34 was identified using the information on their binding affinities to HLA-A24. After the in vitro stimulation of T-cells by dendritic cells (DCs) loaded with these peptide, CTL was successfully established using TOM34-299 (KL-RQEVKQNL (SEQ ID No.7)). This CTLs showed potent cytotoxic activity against the colorectal carcinoma cells. Furthermore, CTL clones and lines derived from these cells also showed specific cytotoxicity against HLA-A24 positive colorectal carcinoma cell lines endogenously over-expressing TOM34. The cytotoxic activities of these CTL clones and lines were not shown against the cell lines lacking expression of either HLA-A24 or a target TAA. Specific cytotoxic activities of these CTL clones and lines were significantly inhibited by the cold target. These results demonstrate that TOM34 is useful as TAAs of CRC and that TOM34 is epitope peptides of TAA restricted by HLA-A24. Since TOM34 antigen is over-expressed in most of CRC and is associated with tumor cell proliferation, they are good targets to be used for immunotherapy against CRC.

Accordingly, the present invention further provides methods of treating or preventing CRC, said methods comprise steps of administering a immunogenic peptide of less than about 40 amino acids, often less than about 20 amino acids, usually less than about 15 amino acids comprising the amino acid sequence of SEQ ID NO: 7. Alternatively, the immunogenic peptide may comprise a derivative of sequence of SEQ ID NO: 7 in which 1, 2, 3, or several amino acids are modified, substituted or added. In preferred embodiments, the immunogenic peptide is a nonapeptide or a decapeptide. Alternatively, the present invention provides a method of inducing anti-tumor immunity for CRC, said method comprises steps of administering an immunogenic peptide of the invention comprising the amino acid sequence of SEQ ID NO: 7 or a derivative thereof as described above. In the present invention, the peptide or derivative thereof can be administered to a subject via in vivo or ex vivo. Furthermore, the present invention also provides use of decapeptide comprising the amino acid sequence of SEQ ID NO: 7 or a derivative thereof for manufacturing an immunogenic composition for treating or preventing CRC.

Homology analysis of TOM34 showed that they do not have significant homology with the peptides derived from any known human gene products. This lowers the possibility of unknown or undesirable immune responses with immunotherapy against these molecules.

Regarding HLA antigens, the use of A-24 type that are highly expressed among the Japanese is favorable for obtaining effective results, and the use of subtypes such as A-2402 are even more preferable. Typically, in the clinic, the type of HLA antigen of the patient requiring treatment is investigated in advance, which enables appropriate selection of peptides having high levels of binding affinity to this antigen, or having cytotoxic T cell (CTL) inducibility by antigen presentation. Furthermore, in order to obtain peptides showing high binding affinity and CTL inducibility, substitution or addition of 1, 2, 3, 4 or several amino acids may be performed based on the amino acid sequence of the naturally occurring TOM34 partial peptide. Herein, the term "several" means 5 or less, or preferably 3 or less. Furthermore, in addition to peptides that are naturally displayed, since the regularity of the sequences of peptides displayed by binding to HLA antigens is already known (Kubo, et al., J. Immunol., 152, 3913, 1994; Rammensee, et al., Immunogenetics. 41:178-228, 1995; Kondo, et al., J. Immunol. 155:4307-12, 1995), modifications based on such regularity can be performed on the immunogenic peptides of the invention. For example, peptides showing high HLA-24 binding affinity have their second amino acid from the N terminus substituted with phenylalanine, tyrosine, methionine, or tryptophan, and peptides whose amino acid at the C terminus is substituted with phenylalanine, leucine, isoleucine, tryptophan, or methionine may also be used favorably.

However, when the peptide sequence is identical to a portion of the amino acid sequence of an endogenous or exogenous protein having a different function, side effects such as autoimmune disorders or allergic symptoms against specific substances may be induced, therefore, preferably, situations in which the sequence matches the amino acid sequence of another protein is avoided by performing a homology search using available databases. Furthermore, if it is clear from homology searches that not even peptides in which 1 or 2 amino acids are different exist, there is no danger that modifications of the above-mentioned amino acid sequence in order to increase the binding affinity with HLA antigens, and/or increase the CTL inducibility will cause such problems.

Although peptides having high binding affinity to the HLA antigens as described above are expected to be highly effective as cancer vaccines, the candidate peptides, which are selected according to the presence of high binding affinity as an indicator, must be examined for the actual presence of CTL inducibility. Confirmation of CTL inducibility is accomplished by inducing antigen-presenting cells carrying human MHC antigens (for example, B-lymphocytes, macrophages, and dendritic cells), or more specifically dendritic cells derived from human peripheral blood mononuclear leukocytes, and after stimulation with the peptides, mixing with CD8-positive cells, and then measuring the cytotoxic activity against the target cells. As the reaction system, transgenic animals that have been produced to express a human HLA antigen (for example, those described in BenMohamed L., et al., Hum. Immunol. 2000 August; 61(8):764-79) may be used. For example, the target cells can be radiolabeled with $^{51}Cr$ and such, and cytotoxic activity can be calculated from radioactivity released from the target cells. Alternatively, it can be examined by measuring IFN-γ produced and released by CTL in the presence of antigen-presenting cells that carry immobilized peptides, and visualizing the inhibition zone on the media using anti-IFN-γ monoclonal antibodies.

As a result of examining the CTL inducibility of peptides as described above, those having high binding affinity to an HLA antigen did not necessarily have high inducibility. Furthermore, decapeptide comprising the amino acid sequences indicated by KLRQEVKQNL (SEQ ID No.7) showed particularly high CTL inducibility.

As noted above, the present invention provides peptides having cytotoxic T cell inducibility, and comprising the amino acid sequence of SEQ ID NO: 7 in which 1, 2, or several amino acids are substituted or added. The amino acid sequence comprising 9 or 10 amino acids indicated in SEQ ID NO: 7 in which 1, 2, or several amino acids are substituted or added preferably do not match the amino acid sequence of other proteins. In particular, amino acid substitution to phenylalanine (F), tyrosine (Y), methionine (M), or tryptophan (W) at the second amino acid from the N terminus, and to phenylalanine (F), leucine (L), isoleucine (I), tryptophan (W), or methionine (M) at the C-terminal amino acid, and amino acid addition of 1 to 2 amino acids at the N terminus and/or C terminus are favorable examples. Specifically, the present invention provides a decapeptide comprising the amino acid sequence KLRQEVKQNL (SEQ ID NO: 7), or K-[L, F, Y, M, or W]-RQEVKQN-[F, L, I, W, or M](SEQ ID NO:62).

Peptides of the invention can be prepared using well known techniques. For example, the peptides can be prepared synthetically, by recombinant DNA technology or chemical synthesis. Peptide of the invention may be synthesized individually or as longer polypeptides comprising two or more peptides. The peptide are preferably isolated i.e., substantially free of other naturally occurring host cell proteins and fragments thereof.

The peptides may contain modifications such as glycosylation, side chain oxidation, or phosphorylation; so long as the modifications do not destroy the biological activity of the peptides as described herein. Other modifications include incorporation of D-amino acids or other amino acid mimetics that can be used, for example, to increase serum half life of the peptides.

The peptides of this invention can be prepared in a combination, which comprises 2 or more of peptides of the invention, for use as a cancer vaccine that may induce CTL in vivo. The peptides may be in a cocktail or may be conjugated to each other using standard techniques. For example, the peptides can be expressed as a single polypeptide sequence. The peptides in the combination may be the same or different. By administering the peptides of this invention, the peptides are presented at a high density on the HLA antigens of antigen-presenting cells, then CTL that specifically react toward the complex formed between the displayed peptide and the HLA antigen are induced. Alternatively, antigen presenting cells that have immobilized the peptides of this invention on their cell surface are obtained by removing dendritic cells from the subjects, these are stimulated by the peptides of this invention, CTL is induced in the subjects by readministering these cells to the subjects, and as a result, aggressiveness towards the target cells can be increased.

More specifically, the present invention provides drugs for treating tumors or preventing proliferation, metastasis, and such of tumors, which comprise 1 or more of peptides of this invention. The peptides of this invention can be used for treating CRC.

The peptides of this invention can be administered directly as a pharmaceutical composition that has been formulated by conventional formulation methods. In such cases, in addition to the peptides of this invention, carriers, excipients, and such that are ordinarily used for drugs can be included as appropriate without particular limitations. The immunogenic compositions of this invention may be used for treatment and prevention of CRC.

The immunogenic compositions for treatment and/or prevention of CRC, which comprise the peptides of this invention as the active ingredients, can comprise an adjuvant so that cellular immunity will be established effectively, or they may be administered with other active ingredients such as antitumor agents, and they may be administered by formulation into granules. An adjuvant that may be applied includes those described in the literature (Johnson, Clin. Microbiol. Rev., 7: 277-289, 1994). Exemplary adjuvants include, aluminum phosphate, aluminum hydroxide, or alum. Furthermore, liposome formulations, granular formulations in which the drug is bound to few-μm diameter beads, and formulations in which a lipid is bound to the peptide may be conveniently used. The method of administration may be oral, intradermal, subcutaneous, intravenous injection, or such, and systemic administration or local administration to the vicinity of the targeted tumor is possible. The dose of the peptides of this invention can be adjusted appropriately according to the disease to be treated, age of the patient, weight, method of administration, and such, and is ordinarily 0.001 mg to 1000 mg, preferably 0.01 mg to 100 mg, more preferably 0.1 mg to 10 mg, and is preferably administered once in a few days to few months. One skilled in the art can appropriately select the suitable dose.

Alternatively, the present invention provides intracellular vesicles called exosomes, which present complexes formed between the peptides of this invention and HLA antigens on their surface. Exosomes can be prepared, for example by using the methods described in detail in Published Japanese Translation of International Publication Nos. Hei 11-510507 and 2000-512161, and is preferably prepared using antigen presenting cells obtained from subjects who are targets of treatment and/or prevention. The exosomes of this invention can be inoculated as cancer vaccines, similarly to the peptides of this invention.

The type of HLA antigens used must match that of the subject requiring treatment and/or prevention. For example, for Japanese, HLA-A24, particularly HLA-A2402 is often appropriate.

In some embodiments the vaccine compositions of the invention comprise a component which primes cytotoxic T lymphocytes. Lipids have been identified as agents capable of priming CTL in vivo against viral antigens. For example, palmitic acid residues can be attached to the ε- and α-amino groups of a lysine residue and then linked to an immunogenic peptide of the invention. The lipidated peptide can then be administered either directly in a micelle or particle, incorporated into a liposome, or emulsified in an adjuvant. As another example of lipid priming of CTL responses, E. coli lipoproteins, such as tripalmitoyl-S-glycerylcysteinlyseryl-serine (P3CSS) can be used to prime CTL when covalently attached to an appropriate peptide (see, e.g., Deres, et al., Nature 342:561-4, 1989).

The immunogenic compositions of the invention may also comprise nucleic acids encoding the immunogenic peptides disclosed here. See, e.g., Wolff et. al. (1990) Science 247: 1465-1468; U.S. Pat. Nos. 5,580,859; 5,589,466; 5,804,566; 5,739,118; 5,736,524; 5,679,647; and WO 98/04720. Examples of DNA-based delivery technologies include "naked DNA", facilitated (bupivicaine, polymers, peptide-mediated) delivery, cationic lipid complexes, and particle-mediated ("gene gun") or pressure-mediated delivery (see, e.g., U.S. Pat. No. 5,922,687).

The immunogenic peptides of the invention can also be expressed by viral or bacterial vectors. Examples of expression vectors include attenuated viral hosts, such as vaccinia or fowlpox. This approach involves the use of vaccinia virus, e.g., as a vector to express nucleotide sequences that encode the peptide. Upon introduction into a host, the recombinant vaccinia virus expresses the immunogenic peptide, and thereby elicits an immune response. Vaccinia vectors and methods useful in immunization protocols are described in, e.g., U.S. Pat. No. 4,722,848. Another vector is BCG (Bacille Calmette Guerin). BCG vectors are described in Stover, et al. (1991) Nature 351:456-460. A wide variety of other vectors useful for therapeutic administration or immunization e.g., adeno and adeno-associated virus vectors, retroviral vectors, Salmonella typhi vectors, detoxified anthrax toxin vectors, and the like, will be apparent. See, e.g., Shata, et al. (2000) Mol. Med. Today 6:66-71; Shedlock, et al. (2000) J. Leukoc. Biol. 68:793-806; and Hipp, et al. (2000) In Vivo 14: 571-85.

The present invention also provides methods of inducing antigen-presenting cells using the peptides of this invention. The antigen-presenting cells can be induced by inducing dendritic cells from the peripheral blood monocytes and then contacting (stimulating) them with the peptides of this invention in vitro, ex vivo or in vivo. When the peptides of this invention are administered to the subjects, antigen-presenting cells that have the peptides of this invention immobilized to them are induced in the body of the subject. Alternatively, after immobilizing the peptides of this invention to the antigen-presenting cells, the cells can be administered to the subject as a vaccine. For example, the ex vivo administration may comprise steps of:
  a: collecting antigen presenting cells from subject, and
  b: contacting with the antigen presenting cells of step a, with the peptide.

The antigen presenting cells obtained by step b can be administered to the subject as a vaccine.

This invention also provides a method for inducing antigen-presenting cells having a high level of cytotoxic T cell inducibility, in which the method comprises the step of transferring genes comprising polynucleotides that encode the peptides of this invention to antigen-presenting cells in vitro. The introduced genes may be in the form of DNAs or RNAs. For the method of introduction, without particular limitations, various methods conventionally performed in this field, such as lipofection, electroporation, and calcium phosphate method may be used. More specifically, it may be performed as described in Reeves, et al., Cancer Res., 56:5672, 1996; Butterfield, et al., J. Immunol., 161:5607, 1998; Boczkowski, et al., J. Exp. Med., 184:465, 1996; Published Japanese Translation of International Publication No. 2000-509281. By transferring the gene into antigen-presenting cells, the gene undergoes transcription, translation, and such in the cell, and then the obtained protein is processed by MHC Class I or Class II, and proceeds through a presentation pathway to present partial peptides.

Furthermore, the present invention provides methods for inducing CTL using the peptides of this invention. When the peptides of this invention are administered to a subject, CTL is induced in the body of the subject, and the strength of the immune system targeting the CRC cells in the tumor tissues is enhanced. Alternatively, they may be used for an ex vivo therapeutic method, in which subject-derived antigen-presenting cells, and CD8-positive cells, or peripheral blood mononuclear leukocytes are contacted (stimulated) with the peptides of this invention in vitro, and after inducing CTL, the cells are returned to the subject. For example, the method may comprise steps of:
  a: collecting antigen presenting cells from subject,
  b: contacting with the antigen presenting cells of step a, with the peptide,
  c: mixing the antigen presenting cells of step b with $CD^{8+}$ T cells, and co-culturing for inducing cytotoxic T-cells, and
  d: collecting $CD^{8+}$ T cells from the co-culture of step c.

The $CD^{8+}$ T cells having cytotoxic activity obtained by step d can be administered to the subject as a vaccine. Accordingly, the present invention relates to CD8+ cells which are capable of recognizing the peptides described herein which are presented by MHC molecules, e.g. HLA-24. Furthermore, the present invention also relates to cells, e.g., APCs comprising an MHC-class I type HLA-24 molecule which presents the peptide described herein.

Furthermore, the present invention provides isolated cytotoxic T cells that are induced using the peptides of this invention. The cytotoxic T cells, which have been induced by stimulation from antigen-presenting cells that present the peptides of this invention, are preferably derived from subjects who are targets of treatment and/or prevention, and can be administered by themselves or in combination with other drugs including the peptides of this invention or exosomes for the purpose of antitumor effects. The obtained cytotoxic T cells act specifically against target cells presenting the peptides of this invention, or preferably the same peptides used for induction. The target cells may be cells that express TOM34 endogenously, or cells that are transfected with TOM34 genes, and cells that present the peptides of this invention on the cell surface due to stimulation by these peptides can also become targets of attack.

The present invention also provides antigen-presenting cells that comprise presentation of complexes formed between HLA antigens and the peptides of this invention. The antigen-presenting cells that are obtained by contacting the peptides of this invention, or the nucleotides encoding the peptides of this invention are preferably derived from subjects who are the targets of treatment and/or prevention, and can be administered as vaccines by themselves or in combination with other drugs including the peptides of this invention, exosomes, or cytotoxic T cells.

In the present invention, the phrase "vaccine" (also referred to as an immunogenic composition) refers to a substance that has the function to induce anti-tumor immunity or immunity to suppress CRC upon inoculation into animals. According to the present invention, polypeptides comprising the amino acid sequence of SEQ ID NO: 7 was suggested to be HLA- A24 restricted epitope peptides that may induce potent and specific immune response against CRC cells expressing TOM34. Thus, the present invention also encompasses method of inducing anti-tumor immunity using polypeptides comprising the amino acid sequence of SEQ ID NO: 7. In general, anti-tumor immunity includes immune responses such as follows:

induction of cytotoxic lymphocytes against tumors comprising cells expressing TOM34,
   induction of antibodies that recognize tumors comprising cells expressing TOM34, and
   induction of anti-tumor cytokine production.

Therefore, when a certain protein induces any one of these immune responses upon inoculation into an animal, the protein is decided to have anti-tumor immunity inducing effect. The induction of the anti-tumor immunity by a protein can be detected by observing in vivo or in vitro the response of the immune system in the host against the protein.

For example, a method for detecting the induction of cytotoxic T lymphocytes is well known. A foreign substance that enters the living body is presented to T cells and B cells by the action of antigen presenting cells (APCs). T cells that respond to the antigen presented by APC in antigen specific manner differentiate into cytotoxic T cells (or cytotoxic T lymphocytes; CTLs) due to stimulation by the antigen, and then proliferate (this is referred to as activation of T cells). Therefore, CTL induction by a certain peptide can be evaluated by presenting the peptide to a T cell by APC, and detecting the induction of CTL. Furthermore, APCs have the effect of activating CD4+ T cells, CD8+ T cells, macrophages, eosinophils and NK cells. Since CD4+ T cells are also important in anti-tumor immunity, the anti-tumor immunity inducing action of the peptide can be evaluated using the activation effect of these cells as indicators.

A method for evaluating the inducing action of CTL using dendritic cells (DCs) as APC is well known in the art. DC is a representative APC having the strongest CTL inducing action among APCs. In this method, the test polypeptide is initially contacted with DC and then this DC is contacted with T cells. Detection of T cells having cytotoxic effects against the cells of interest after the contact with DC shows that the test polypeptide has an activity of inducing the cytotoxic T cells. Activity of CTL against tumors can be detected, for example, using the lysis of $^{51}$Cr-labeled tumor cells as the indicator. Alternatively, the method of evaluating the degree of tumor cell damage using $^{3}$H-thymidine uptake activity or LDH (lactose dehydrogenase)-release as the indicator is also well known.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The test polypeptides confirmed to possess CTL inducing activity by these methods are polypeptides having DC activation effect and subsequent CTL inducing activity. Therefore, polypeptides that induce CTL against tumor cells are useful as vaccines against CRC. Furthermore, APC that acquired the ability to induce CTL against CRC by contacting with the polypeptides are useful as vaccines against CRC. Furthermore, CTL that acquired cytotoxicity due to presentation of the polypeptide antigens by APC can be also used as vaccines against CRC. Such therapeutic methods for CRC using anti-tumor immunity due to APC and CTL are referred to as cellular immunotherapy.

Generally, when using a polypeptide for cellular immunotherapy, efficiency of the CTL-induction is known to increase by combining a plurality of polypeptides having different structures and contacting them with DC. Therefore, when stimulating DC with protein fragments, it is advantageous to use a mixture of multiple types of fragments.

Alternatively, the induction of anti-tumor immunity by a polypeptide can be confirmed by observing the induction of antibody production against tumors. For example, when antibodies against a polypeptide are induced in a laboratory animal immunized with the polypeptide, and when growth, proliferation or metastasis of tumor cells is suppressed by those antibodies, the polypeptide can be determined to have an ability to induce anti-tumor immunity.

Anti-tumor immunity is induced by administering the vaccine of this invention, and the induction of anti-tumor immunity enables treatment and prevention of CRC. Therapy against or prevention of the onset of CRC includes any of the steps, such as inhibition of the growth of CRC cells, involution of CRC cells and suppression of occurrence of CRC cells. Decrease in mortality of individuals having CRC, decrease of CRC markers in the blood, alleviation of detectable symptoms accompanying CRC and such are also included in the therapy or prevention of CRC. Such therapeutic and preventive effects are preferably statistically significant. For example, in observation, at a significance level of 5% or less, wherein the therapeutic or preventive effect of a vaccine against CRC is compared to a control without vaccine administration. For example, Student's t-test, the Mann-Whitney U-test or ANOVA may be used for statistical analyses.

The above-mentioned protein having immunological activity, or a polynucleotide or vector encoding the protein may be combined with an adjuvant. An adjuvant refers to a compound that enhances the immune response against the protein when administered together (or successively) with the protein having immunological activity. Examples of adjuvants include cholera toxin, *salmonella* toxin, alum and such, but are not limited thereto. Furthermore, the vaccine of this invention may be combined appropriately with a pharmaceutically acceptable carrier. Examples of such carriers are sterilized water, physiological saline, phosphate buffer, culture fluid and such. Furthermore, the vaccine may contain as necessary, stabilizers, suspensions, preservatives, surfactants and such. The vaccine is administered systemically or locally. Vaccine administration may be performed by single administration or boosted by multiple administrations.

When using APC or CTL as the vaccine of this invention, CRC can be treated or prevented, for example, by the ex vivo method. More specifically, PBMCs of the subject receiving treatment or prevention are collected, the cells are contacted with the polypeptide ex vivo, and following the induction of APC or CTL, the cells may be administered to the subject. APC can be also induced by introducing a vector encoding the polypeptide into PBMCs ex vivo. APC or CTL induced in vitro can be cloned prior to administration. By cloning and growing cells having high activity of damaging target cells, cellular immunotherapy can be performed more effectively. Furthermore, APC and CTL isolated in this manner may be used for cellular immunotherapy not only against individuals from whom the cells are derived, but also against similar types of diseases in other individuals.

Pharmaceutical Compositions for Inhibiting CRC:

In the context of the present invention, suitable pharmaceutical formulations include those suitable for oral, rectal, nasal, topical (including buccal and sub-lingual), vaginal or parenteral (including intramuscular, sub-cutaneous and intravenous) administration, or for administration by inhalation or insufflation. Preferably, administration is intravenous. The formulations are optionally packaged in discrete dosage units.

Pharmaceutical formulations suitable for oral administration include capsules, cachets or tablets, each containing a predetermined amount of active ingredient. Suitable formulations also include powders, granules, solutions, suspensions and emulsions. The active ingredient is optionally administered as a bolus electuary or paste. Tablets and capsules for oral administration may contain conventional excipients, such as binding agents, fillers, lubricants, disintegrant and/or wetting agents. A tablet may be made by compression or molding, optionally with one or more formulational ingredients. Compressed tablets may be prepared by compressing in a suitable machine the active ingredients in a free-flowing form, such as a powder or granules, optionally mixed with a binder, lubricant, inert diluent, lubricating, surface active and/or dispersing agent. Molded tablets may be made by molding in a suitable machine a mixture of the powdered compound moistened with an inert liquid diluent. The tablets may be coated according to methods well known in the art. Oral fluid preparations may be in the form of, for example, aqueous or oily suspensions, solutions, emulsions, syrups or elixirs, or may be presented as a dry product for constitution with water or other suitable vehicle before use. Such liquid preparations may contain conventional additives, such as suspending agents, emulsifying agents, non-aqueous vehicles (which may include edible oils), and/or preservatives. The tablets may optionally be formulated so as to provide slow or controlled release of the active ingredient therein. A package of tablets may contain one tablet to be taken on each of the month.

Formulations suitable for parenteral administration include aqueous and non-aqueous sterile injection solutions, optionally contain anti-oxidants, buffers, bacteriostats and solutes which render the formulation isotonic with the blood of the intended recipient; as well as aqueous and non-aqueous sterile suspensions including suspending agents and/or thickening agents. The formulations may be presented in unit dose or multi-dose containers, for example as sealed ampoules and vials, and may be stored in a freeze-dried (lyophilized) condition, requiring only the addition of the sterile liquid carrier, for example, saline, water-for-injection, immediately prior to use. Alternatively, the formulations may be presented for continuous infusion. Extemporaneous injection solutions and suspensions may be prepared from sterile powders, granules and tablets of the kind previously described.

Formulations suitable for rectal administration include suppositories with standard carriers such as cocoa butter or polyethylene glycol. Formulations suitable for topical administration in the mouth, for example, buccally or sublingually, include lozenges, containing the active ingredient in a flavored base such as sucrose and acacia or tragacanth, and pastilles, comprising the active ingredient in a base such as gelatin and glycerin or sucrose and acacia. For intra-nasal administration, the compounds of the invention may be used as a liquid spray, a dispersible powder, or in the form of drops. Drops may be formulated with an aqueous or non-aqueous base also comprising one or more dispersing agents, solubilizing agents and/or suspending agents.

For administration by inhalation the compounds can be conveniently delivered from an insufflator, nebulizer, pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds may take the form of a dry powder composition, for example a powder mix of the compound and a suitable powder base, such as lactose or starch. The powder composition may be presented in unit dosage form, for example, as capsules, cartridges, gelatin or blister packs, from which the powder may be administered with the aid of an inhalator or insufflators.

Other formulations include implantable devices and adhesive patches which release a therapeutic agent.

When desired, the above described formulations, adapted to give sustained release of the active ingredient, may be employed. The pharmaceutical compositions may also contain other active ingredients, such as antimicrobial agents, immunosuppressants and/or preservatives.

It should be understood that in addition to the ingredients particularly mentioned above, the formulations of this invention may include other agents conventional in the art with regard to the type of formulation in question. For example, formulations suitable for oral administration may include flavoring agents.

Preferred unit dosage formulations contain an effective dose, as recited below, or an appropriate fraction thereof, of the active ingredient.

For each of the aforementioned conditions, the compositions, e.g., polypeptides and organic compounds, can be administered orally or via injection at a dose ranging from about 0.1 to about 250 mg/kg per day. The dose range for adult humans is generally from about 5 mg to about 17.5 g/day, preferably about 5 mg to about 10 g/day, and most preferably about 100 mg to about 3 g/day. Tablets or other unit dosage forms of presentation provided in discrete units may conveniently contain an amount which is effective at such dosage or as a multiple of the same, for instance, units containing about 5 mg to about 500 mg, usually from about 100 mg to about 500 mg.

The dose employed will depend upon a number of factors, including the age and sex of the subject, the precise disorder being treated, and its severity. Also the route of administration may vary depending upon the condition and its severity. In any event, appropriate and optimum dosages may be routinely calculated by those skilled in the art, taking into consideration the above-mentioned factors.

Aspects of the present invention are described in the following examples, which are not intended to limit the scope of the invention described in the claims. The following examples illustrate the identification and characterization of genes differentially expressed in CRC cells.

EXAMPLES

Cell Lines and Clinical Materials

Human colon cancer cell lines HCT116 and RKO were obtained from the American Type Culture Collection (Rockville, Md.). All these cells were cultured as monolayers in appropriate media, McCoys 5A (Invitrogen, Carlsbad, Calif.) for HCT116 and RPMI 1640 (Sigma-Aldrich Corporation, St. Louis, Mo.) for RKO, supplemented with 10% fetal bovine serum (Cansera International Inc., Ontario, Canada) and 1% antibiotic/antimycotic solution (Sigma-Rich). Cells were maintained at 37° C. in an atmosphere of humidified air with 5% $CO_2$. Cancerous tissues and corresponding noncancerous mucosae were excised from 12 patients during surgery, after informed consent had been obtained.

TISI cells (HLA-A24/24) and EHM (HLA-A3/3), human B-lymphoblastoid cell lines, were generous gifts from Takara Shuzo Co, Ltd. (Otsu, Japan). The TISI cells were used for peptide-mediated cytotoxicity assays. Colorectal carcinoma cell lines DLD-1 (HLA-A24/02), HT29 (HLA-A24/01) and SNU-C2A (HLA-A31/26) were purchased from ATCC. A chronic myelogenous leukemia cell line K562 was purchased from ATCC.

Semiquantitative RT-PCR

Total RNA was extracted from cultured cells or clinical tissues using TRIZOL reagent (Invitrogen) according to the manufacturer's protocol. Extracted RNA was treated with DNaseI (Roche Diagnostics, Mannheim, Germany) and reverse transcribed to single-stranded cDNAs using oligo $(dT)_{12-18}$ (SEQ ID NO: 65) primer and Superscript II reverse transcriptase (Invitrogen). We prepared appropriate dilutions of each single-stranded cDNA for subsequent PCR amplification by monitoring the GAPDH gene as a quantitative control. Primer sequences used are, 5'-ACAACAGCCTCAA-GATCATCAG-3' (SEQ ID NO; 41) and 5'-GGTCCACCACTGACACGTTG-3' (SEQ ID NO; 42) for GAPDH, 5'-TGGTATAAACCTAAGGCCCTGAT-3' (SEQ ID NO; 43) and 5'-TAAACAGCTTAGGTGCCTCTCTG-3' (SEQ ID NO; 44) for TOM34. All of the amplification reactions were preceded by initial denaturation at 94° C. for 2 min, followed by 18 (for GAPDH) or 29 cycles (for TOM34) of amplification at 94° C. for 30 s, 60° C. for 30 s, and 72° C. for 30 s on a GeneAmp PCR system 9700 (PE Applied Biosystems, Foster, Calif.).

Northern Blotting

Human multiple-tissue blots (BD Bioscience, Palo Alto, Calif.) were hybridized with a $^{32}$P-labeled PCR product of TOM34. The probe was prepared by RT-PCR using a set of primers, 5'-GAACGTGAAGGCATTCTACAGA-3' (SEQ ID NO; 45) and 5'-TAAACAGCTTAGGTGCCTCTCTG-3' (SEQ ID NO; 44), and subsequent random-oligonucleotide labeling with $^{32}$P-dCTP with a Mega Label kit (Amersham Biosciences, Buckinghamshire, United Kingdom). Prehybridization, hybridization, and washing were performed according to the supplier's recommendations. The blots were autoradiographed with intensifying screens at −80° C. for 10 days.

Preparation of Polyclonal Antibody Against TOM34

The entire coding region of TOM34 was amplified using a set of primers, 5'-CATAAGCTTGCATGGCCCCCAAAT-TCCCA-3' (SEQ ID NO; 58) and 5'-GTTAAGCTTTTAGT-GTAGGTTCT-3', (SEQ ID NO; 59) and subsequently cloned into an appropriate cloning site of pET28 vector (Novagen, Madison, Wis.) to generate plasmids expressing His-tagged TOM34 protein. The recombinant protein was expressed in *Escherichia coli*, BL21-CodonPlus (DE3)-RIL strain (Stratagene, LaJolla, Calif.), and purified using TALON Superflow Metal Affinity Resin (BD Bioscience) according to the manufacture's protocol. The protein was inoculated into rabbits, and the immunized sera were purified on affinity columns according to the standard method. Western blot analysis was carried out using proteins extracted from the cells using 0.1% RIPA like buffer containing 50 mM Tris-HCl (pH7.5), 250 mM NaCl, 0.1% SDS, and 0.5% NP40 with Protease Inhibitor Cocktail Set III (CALBIOCHEM, La Jolla, Calif.).

Immunohistochemistry

Immunohistochemical staining was performed using affinity-purified polyclonal antibody against human TOM34. The paraffin-embedded tissue sections were subjected to the SAB-PO peroxidase immunostaining system (Nichirei, Tokyo, Japan), after antigens were retrieved from deparaffinized and re-hydrated tissues by pre-treating the slides in 0.01M citrate buffer (pH6.0) at 108° C. for 10 min by autoclave.

Construction of psiU6BX Expressing siRNAs to TOM34

Plasmids expressing siRNAs were prepared by cloning double-stranded oligonucleotides into the BbsI site in the psiU6BX vector as described previously (WO2004/076623). The sequences of paired oligonucleotides are; 5'-CAC-CGAAAGTGTTCTCTACTCCATTCAA-GAGATGGAGTAGAGAACACTTTC-3' (SEQ ID NO; 46) and 5'-AAAAGAAAGTGTTCTCTACTCCATCTCT-TGAATGGAGTAGAGAACACTTTC-3' (SEQ ID NO; 47) for siD; 5'-CACCGGATGGAAACTGCAGAGACTTCAA-GAGAGTCTCTGCAGTTTCCATCC-3' (SEQ ID NO; 50) and 5'-AAAAGGATGGAAACTGCAGAGACTCTCT-TGAAGTCTCTGCAGTTTCCATCC-3' (SEQ ID NO; 51) for siE;

After phosphorylated with T4-polynucleotide kinase, the paired oligonucleotides were boiled for five min, and were subsequently annealed to produce double-stranded oligonucleotides by cooling down slowly. A control plasmid, psiU6BX-EGFP was prepared using ologonucleotide consisting of the following sequences. Each nucleotide sequences, target sequences of the siRNA, and SEQ ID NOs are shown in table 1. 5'-CACCGAAGCAGCACGACTTCT-TCTTCAAGAGAGAAGAAGTCGTGCTGCTTC-3' (SEQ ID NO; 54) and 5'-AAAAGAAGCAGCACGACTTCT-TCTCTCTTGAAGAAGAAGTCGTGCTGCTTC-3' (SEQ ID NO; 55).

To examine the effect of TOM34-siRNAs, western blotting analysis was carried out using anti-TOM34 antibody five days after transfection with the plasmids.

Table 1. Sequence of specific double-stranded oligonucleotide inserted into siRNA expression vector and target sequences of each siRNAs.

|  |  | SEQ ID NO | sequence |
|---|---|---|---|
| TOM34 siD position 288-306 | insert seq | 46 | CACCGAAAGTGTTCTCTACTCCATTCAAG AGATGGAGTAGAGAACACTTTC |
|  | insert seq | 47 | AAAAGAAAGTGTTCTCTACTCCATCTCTT GAATGGAGTAGAGAACACTTTC |
|  | target | 48 | GAAAGTGTTCTCTACTCCA |
|  | hairpin siRNA | 49 | GAAAGTGTTCTCTACTCCATTCAAGAGAT GGAGTAGAGAACACTTTC |
| TOM34 siE position 329-347 | insert seq | 50 | CACCGGATGGAAACTGCAGAGACTTCAA GAGAGTCTCTGCAGTTTCCATCC |
|  | insert seq | 51 | AAAAGGATGGAAACTGCAGAGACTCTCT TGAAGTCTCTGCAGTTTCCATCC |
|  | target | 52 | GGATGGAAACTGCAGAGAC |
|  | hairpin siRNA | 53 | GGATGGAAACTGCAGAGACTTCAAGAGA GTCTCTGCAGTTTCCATCC |
| EGFP control | insert seq | 54 | CACCGAAGCAGCACGACTTCTTCTTCAAG AGAGAAGAAGTCGTGCTGCTTC |
|  | insert seq | 55 | AAAAGAAGCAGCACGACTTCTTCTCTCTT GAAGAAGAAGTCGTGCTGCTTC |
|  | target | 56 | GAAGCAGCACGACTTCTTC |
|  | hairpin siRNA | 57 | GAAGCAGCACGACTTCTTCTCTCTTGAAG AAGAAGTCGTGCTGCTTC |

Colony-formation Assay

HCT116 cells plated on 10-cm dish ($4\times10^5$ cells/dish) were transiently transfected with plasmids expressing TOM34-siRNAs using FuGENE6 reagent (Roche Diagnostics), and maintained in a medium containing 10% fetal bovine serum with 800 μg/ml Geneticin for two weeks. The surviving cells were fixed with 100% methanol and stained with Giemsa solution. In another experiment, the viable cells were measured with a cell-counting kit (DOJINDO, kumamoto, Japan).

Statistical Analysis

Statistical significance was analyzed by ANOVA with Scheffes F test, using commercially available software (Statview; SAS Institute, Cary, N.C.)

Peptide Derived from TOM34

Nonamer and 10-mer peptides derived from the TOM34 peptide sequence that would bind to HLA-A24 molecule were predicted by the binding prediction software (on the world wide web at www.bimas.dcrt.nih.gov/cgi-bin/molbio/ken_parker_comboform) (Parker K C, et. al., J Immunol. 1994; 152(1):163-75). These peptides were synthesized by Mimotopes, San Diego, Calif., according to the standard solid phase synthesis method and purified by reversed phase HPLC. The purity (>90%) and the identity of the peptides were determined by analytical HPLC and mass spectrometry analysis, respectively. Peptides were dissolved in dimethylsulfoxide (DMSO) at 20 mg/ml and stored at −80° C.

In Vitro CTL Induction

Monocyte-derived dendritic cells (DCs) were used as antigen-presenting cells (APCs) to induce CTLs against peptides presented on HLA. DCs were generated in vitro as described elsewhere (Nukaya I, et al., Int J Cancer. 1999; 80(1):92-7; Tsai V, et al., J Immunol. 1997; 158(4):1796-802). Briefly, peripheral blood mononuclear cells (PBMCs) were isolated from normal volunteers ((HLA-A24) by Ficoll-Paque (Pharmacia) solution and separated by adherence to a plastic tissue culture flask (Becton Dickinson) so as to enrich them for the monocyte fraction. The monocyte-enriched population was cultured in the presence of 1,000 U/ml of GM-CSF (provided by Kirin Brewery Company) and 1,000 U/ml of IL-4 (Genzyme) in AIM-V (Invitrogen) containing 2% heat-inactivated autologous serum (AS). After 7 days in the culture, the cytokine-generated DCs were loaded with 20 µg/ml of HLA-A24-binding peptides in the presence of 3 µg/ml of β2-microglobulin for 4 hrs at 20° C. in AIM-V. These peptide-loaded DCs were then irradiated (5,500 rad) and mixed at a 1:20 ratio with autologous CD8+ T cells, obtained by positive selection with Dynabeads M-450 CD8 (Dynal) and Detachabead (Dynal). This mixture was subdivided and aliquots were incubated in 48-well plates (Corning); each well contained $1.5 \times 10^4$ peptide-loaded DCs and $3 \times 10^5$ CD8+ T cells in 0.5 ml of AIM-V/2% AS containing 10 ng/ml of IL-7 (Genzyme). Three days later, these cultures were supplemented with IL-2 (CHIRON) to a final concentration of 20 IU/ml. On day 7 and 14, the T cells were further restimulated with the autologous peptide-loaded DCs. The DCs were prepared each time by the same way as described above. Cytotoxicity was tested against peptide-loaded TISI cells after the 3rd round of peptide stimulation on day 21.

CTL Expansion Procedure

CTLs were expanded in culture using the method similar to the one described by Riddell, et al. (Walter et al, N Engl J Med 333:1038-1044, (1995), Riddel et al, Nature Med. 2:216-223, (1996)). A total of $5 \times 10^4$ CTLs were resuspended in 25 ml of AIM-V/5% AS with $25 \times 10^6$ irradiated (3,300 rad) PBMC and $5 \times 10^6$ irradiated (8,000 rad) EHM cells in the presence of 40 ng/ml of anti-CD3 monoclonal antibody (Pharmingen). One day after initiating the culture, 120 IU/ml of IL-2 was added to the culture. The culture was fed with fresh AIM-V/5% AS containing 30 IU/ml of IL-2 on days 5, 8 and 11.

Establishment of CTL Clones

The expanded CTL cultures were diluted and the cells were distributed in the wells of 96-well round-bottom microtiter plates (Nalge Nunc International) adjusting the number of the cells to be 0.3, 1, and 3 CTLs/well. CTLs were then cultured with $7 \times 10^4$ cells/well of allogenic PBMCs, $1 \times 10^4$ cells/well of EHM, 30 ng/ml of anti-CD3 antibody, and 125 U/ml of IL-2 in total of 150 µl/well of AIM-V containing 5% AS. 50 µl/well of IL-2 was added to the medium 10 days later so that IL-2 became 125 U/ml in the final concentration. Cytotoxic, activity of CTLs was tested on the 14th day, and CTL clones were expanded using the same method as described above.

Cytotoxicity Assay

Target cells were labeled with 100 µCi of $Na_2{}^{51}CrO_4$ (Perkin Elmer Life Sciences) for 1 hr at 37° C. in a $CO_2$ incubator. Peptide-loaded target cells were prepared by incubating the cells with 20 µg/ml of the peptide for 16 hrs at 37° C. before labeling. Labeled target cells were rinsed and mixed with effector cells in a final volume of 0.2 ml in round-bottom microtiter plates. The plates were centrifuged (4 minutes at 800×g) to increase cell-to-cell contact and placed in a $CO_2$ incubator at 37° C. After 4 hrs of incubation, 0.1 ml of the supernatant was collected from each well and the radioactivity was determined with a gamma counter. In case of evaluating cytotoxicity for target cells that endogenously express TOM34, the cytolytic activity was tested in the presence of 30-fold excess of unlabeled K562 cells to eliminate any non-specific lysis due to NK-like effectors. Antigen specificity was confirmed by the cold target inhibition assay, which utilized unlabeled TISI cells that were loaded with the antigen peptide (20 µg/ml for 16 hrs at 37° C.) to compete for the recognition of $^{51}$Cr-labeled HT29 tumor cells.

The percentage of specific cytotoxicity was determined by calculating the percentage of specific $^{51}$Cr-release by the following formula: {(cpm of the test sample release−cpm of the spontaneous release)/(cpm of the maximum release−cpm of the spontaneous release)}×100. Spontaneous release was determined by incubating the target cells alone, in the absence of effector cells, and the maximum release was obtained by incubating the targets with 1N HCl. All measurements were done in duplicate, and the standard errors of the means were consistently below 10% of the value of the mean.

Results

Elevated Expression of TOM34 in CRCs

Figure 1:
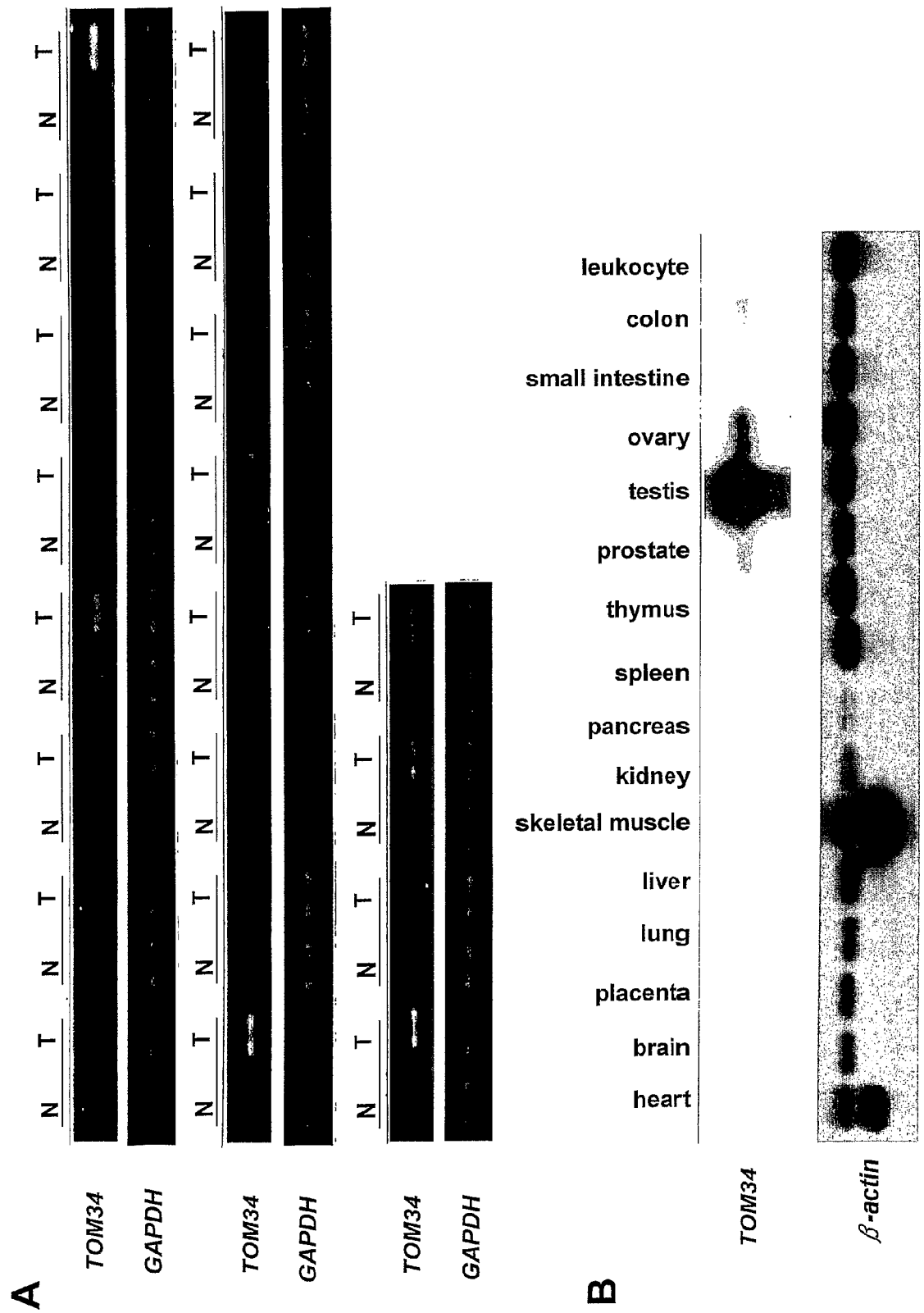
FIG. 1 depicts the expression level of TOM34 gene in various tissues. (A) Semi-quantitative RT-PCR analysis of TOM34 in colon cancer tissues and their corresponding non-cancerous mucosa. T, tumor tissue; N, normal tissue. Expression of GAPDH served as an internal control. (B) Multiple-tissue northern blot analysis of TOM34. The transcript of TOM34 is approximately 2.0-kb by size.

In our earlier study, we identified a number of genes whose expression levels were frequently altered in colon tumors by the genome-wide expression profile analysis of 11 CRCs and nine adenomas of the colon using a cDNA microarray consisting of 23040 genes. Among the genes whose expression levels were frequently up-regulated in the 11 carcinomas, we focused in the present invention on a gene with in-house identification number of D3124, which corresponded to TOM34 (GeneBanck Accession NO: AB085681, SEQ ID NO; 60, 61) (34-kDa Translocase of the Outer Mitochondrial Membrane). Subsequent semi-quantitative RT-PCR analysis revealed its enhanced expression in 16 of 20 CRC clinical samples examined (FIG. 1A). In addition, TOM34 was also significantly up-regulated in all eight hepatocellular carcinomas, five out of 19 lung cancers, 3 out of 9 bladder cancers, seven out of 27 acute myeloid leukemias, and nine out of 49 soft tissue sarcomas in our cDNA microarray data. To investigate its expression in human normal tissues, we performed multiple-tissue Northern blot analysis using TOM34 cDNA as a probe. As a result, the analysis revealed a transcript of approximately 2.0 kb by size, which was abundantly expressed in the testis and ovary, and weakly in the prostate, spleen, and colon, but not expressed in any of 11 other tissues examined (FIG. 1B).

Accumulated TOM34 Protein in Colorectal Cancer Cell Lines and CRC Tissues

Figure 2:
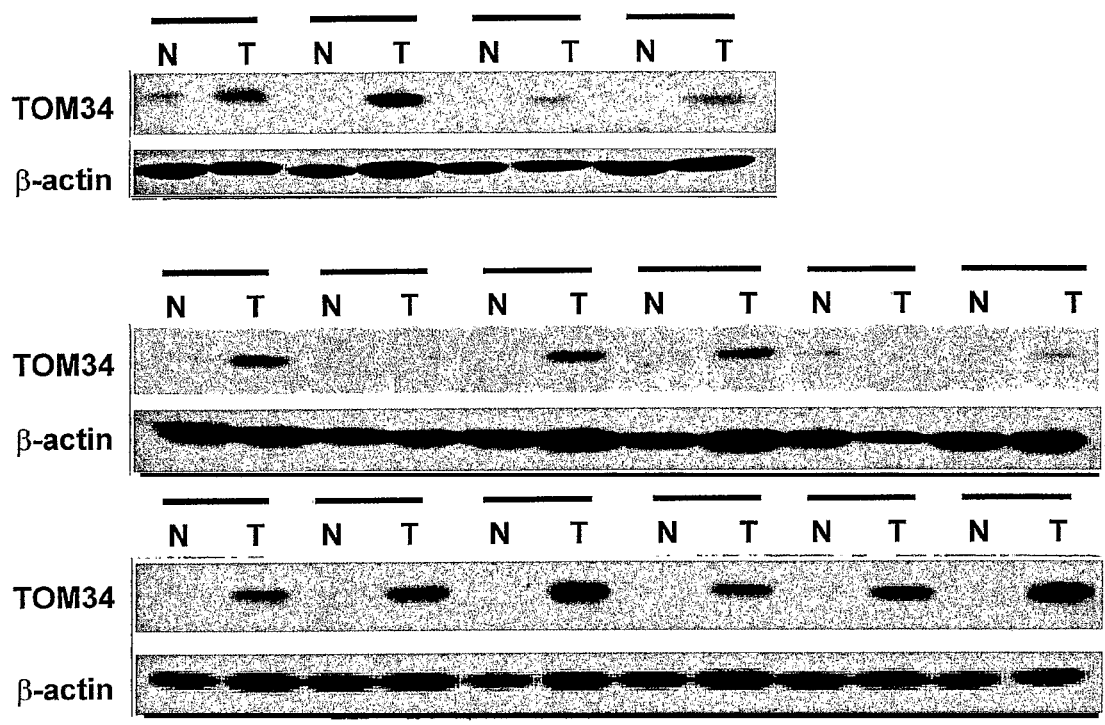
FIG. 2 depicts the expression level of the protein encoded by TOM34 gene in various tissues. (A) Western Blot analysis of TOM34 in colon cancer tissues and their corresponding non-cancerous mucosa. T, tumor tissue; N, normal tissue. (B) Expression of TOM34 in colon cancer cell lines. Expression of beta-actin served as an internal control.
Figure 2:
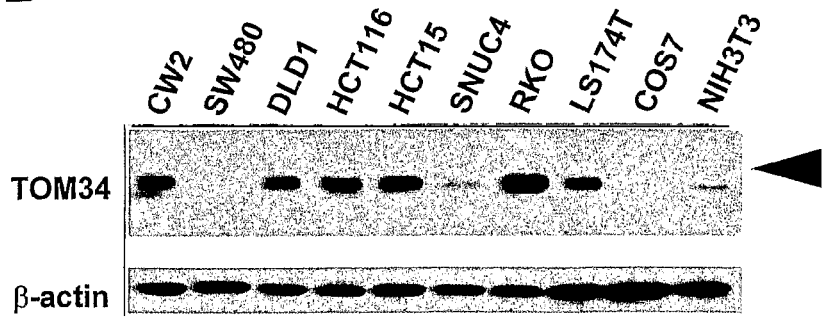
Figure 3:
FIG. 3 depicts a result of immunohistochemical staining of TOM34 in colon cancer tissues. (A and B) Representative images of the staining in cancerous and non-cancerous cells. Magnification: ×40, (C and D) Images of normal mucasa, and cancerous tissues (C normal, D; tumor). Magnification: ×200.
Figure 3:
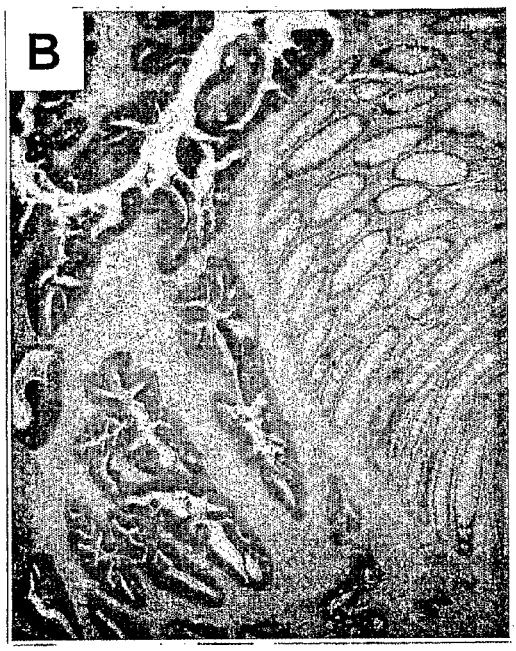
Figure 3:
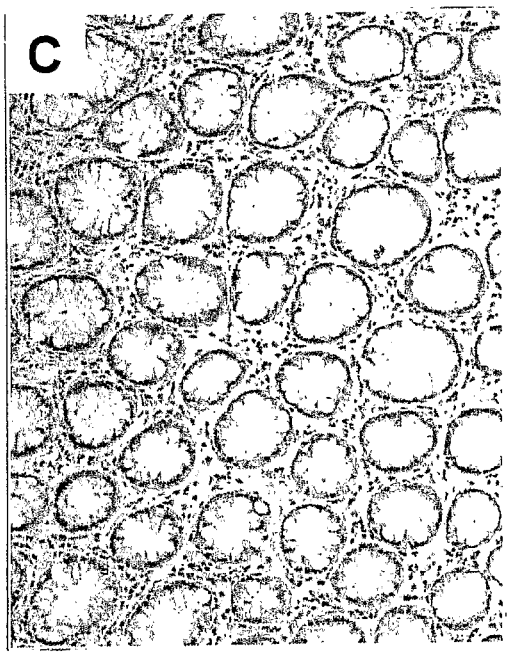
Figure 3:
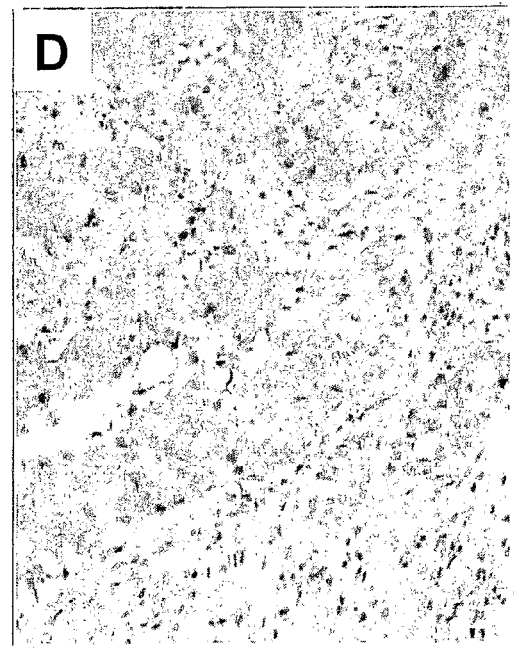

We prepared anti-TOM34 polyclonal antibody and examined expression of TOM34 protein in eight CRC cell lines and 12 CRC tissues by immunohistochemical staining. Immunoblot analysis detected a 34-kDa band of TOM34 that was abundantly expressed in all CRC cell lines examined. On the other hand, low levels of expression were shown in NIH3T3 and COS7, two non-cancerous cell lines (FIG. 2B). Western blot analysis using 16 CRC and corresponding non-cancerous mucosal tissues demonstrated its enhanced expression in 15 out of the 16 tumors compared to the normal mucosa (FIG. 2A). To examine subcellular localization of TOM34, we carried out immunocytochemical staining using HCT116 and RKO cells with the anti-TOM34 antibody, which showed cytoplasmic localization of the protein. In addition, we performed immunohistochemical staining using 12 paraffin-embedded colon cancer tissues. In 11 out of the 12 tumors, TOM34 was strongly stained in the cytoplasms of cancerous cells, but it was barely stained in non-cancerous mucosa (FIG. 3).

Effect of TOM34-siRNAs on Growth of Colon Cancer Cells

Figure 4:
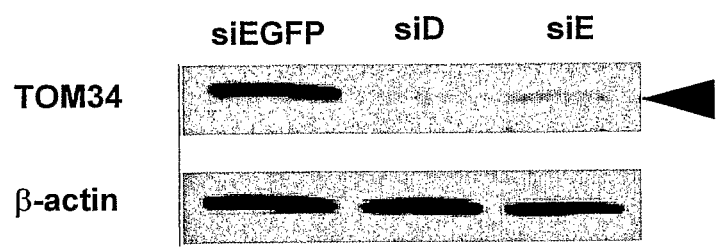
FIG. 4 depicts suppressing effect of TOM34 siRNA on expression of TOM34 gene or cell growth of CRC cell line. (A) Effect of siRNAs on the expression of TOM34 in HCT116 cells. Expression of TOM34 was analyzed by western blot analysis. Expression of beta-actin served as an internal control. EGFP-specific siRNA (siEGFP) was prepared for a negative control. (B) Effect of TOM34-siRNAs on the growth HCT116 cells. Viability of HCT116 cells in response to EGFP-siRNA or TOM34-siRNAs was measured by MTT assay in triplicate. Error bars, SD; Asterisk denotes a significant difference (P<0.0001) determined by a Scheff's F test.
Figure 4:
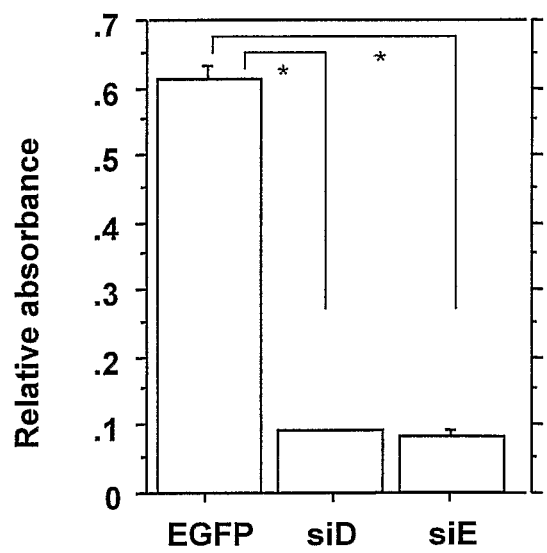

To elucidate the role of TOM34 in cancer cells, we prepared plasmids expressing siRNA to TOM34 and examined their effect on the growth of cancer cells. We prepared two forms of plasmids expressing siRNAs designated to suppress TOM34 (psiU6BX-TOM34-siD, and -siE) and a control plasmid (psiU6BX-siEGFP). We transfected HCT116 cells with psiU6BX-TOM34-siD, psiU6BX-TOM34-siE, or psiU6BX-siEGFP. Western blot analysis of extracts from transfected cells revealed that psiU6BX-TOM34-siD and psiU6BX-TOM34-siE significantly suppressed TOM34 expression in the transfected cells compared to psiU6BX-siEGFP (FIG. 4A). We transfected with the plasmids co-expressing neomycin-resistance gene into HCT116 cells, and cultured them with an appropriate concentration of Geneticin for 13 days. In accordance with reduced expression of TOM34, both psiU6BX-TOM34-siD and psiU6BX-TOM34-siE markedly retarded the growth of transfected cells compared to psiU6BX-siEGFP (FIG. 4B). These data indicated that expression of TOM34 is associated with the growth of cancer cells.

Prediction of HLA-A24 Binding Peptides Derived from TOM34

Tables 2 and 3 show the predicted peptides for the antigen in the order of high binding affinity. Twenty 10-mer peptides (Table 2) and twenty 9-mer peptides (Table 3) were selected for the antigen and examined as described below.

TABLE 2

Prediction of HLA-Class I Epitope Candidates (HLA-A24:10 mer)

| Start Position | Sequence | Binding Score (BIMAS) | SEQ ID NO |
|---|---|---|---|
| 229 | TYSNRALCYL | 200.0 | 1 |
| 53 | LYSNRAACHL | 200.0 | 2 |
| 94 | AYEAKEKYPM | 37.5 | 3 |
| 194 | RVLKEEGNEL | 15.8 | 4 |
| 215 | KYSESLLCSN | 14.4 | 5 |
| 211 | KAIEKYSESL | 14.4 | 6 |

TABLE 2-continued

Prediction of HLA-Class I Epitope Candidates (HLA-A24:10 mer)

| Start Position | Sequence | Binding Score (BIMAS) | SEQ ID NO |
|---|---|---|---|
| 299 | KLRQEVKQNL | 13.4 | 7 |
| 127 | RMTRALMDSL | 9.6 | 8 |
| 242 | QYTEAVKDCT | 8.4 | 9 |
| 80 | LVPFSIKPLL | 8.4 | 10 |
| 278 | KSSFADISNL | 8.0 | 11 |
| 216 | YSESLLCSNL | 7.2 | 12 |
| 79 | ALVPFSIKPL | 7.2 | 13 |
| 279 | SSFADISNLL | 6.7 | 14 |
| 69 | DCIKDCTSAL | 6.0 | 15 |
| 212 | AIEKYSESLL | 6.0 | 16 |
| 245 | EAVKDCTEAL | 6.0 | 17 |
| 22 | NGQYAEASAL | 6.0 | 18 |
| 123 | EGINRMTRAL | 6.0 | 19 |
| 272 | KALKDYKSSF | 6.0 | 20 |

TABLE 3

Prediction of HLA-Class I Epitope Candidates (HLA-A24:9 mer)

| Start Position | Sequence | Binding Score (BIMAS) | SEQ ID NO |
|---|---|---|---|
| 104 | AYVDYKTVL | 360.0 | 21 |
| 31 | LYGRALRVL | 200.0 | 22 |
| 4 | KFPDSVEEL | 79.2 | 23 |
| 276 | DYKSSFADI | 60.0 | 24 |
| 280 | SFADISNLL | 40.3 | 25 |
| 100 | KYPMAYVDY | 15.0 | 26 |
| 215 | KYSESLLCS | 12.0 | 27 |
| 236 | CYLVLKQYT | 10.8 | 28 |
| 141 | RLKLPSIPL | 8.0 | 29 |
| 136 | LGPEWRLKL | 7.9 | 30 |
| 153 | SAQKRWNSL | 7.2 | 31 |
| 195 | VLKEEGNEL | 6.3 | 32 |
| 242 | QYTEAVKDC | 6.0 | 33 |
| 134 | DSLGPEWRL | 6.0 | 34 |
| 24 | QYAEASALY | 6.0 | 35 |
| 54 | YSNRAACHL | 6.0 | 36 |
| 80 | LVPFSIKPL | 6.0 | 37 |

TABLE 3-continued

Prediction of HLA-Class I Epitope Candidates (HLA-A24:9 mer)

| Start Position | Sequence | Binding Score (BIMAS) | SEQ ID NO |
|---|---|---|---|
| 230 | YSNRALCYL | 6.0 | 38 |
| 124 | GINRMTRAL | 6.0 | 39 |
| 212 | AIEKYSESL | 6.0 | 40 |

Stimulation of the T Cells Using the Predicted Peptides

Cytotoxic T cells that recognize the peptides derived from TOM34 were generated in the way described in "Materials and Methods". Resulting CTLs with detectable cytotoxic activity were expanded, and those CTL lines were established that show higher cytotoxic activities against the peptide-loaded target as compared to the target without peptide pulse.

Figure 5:
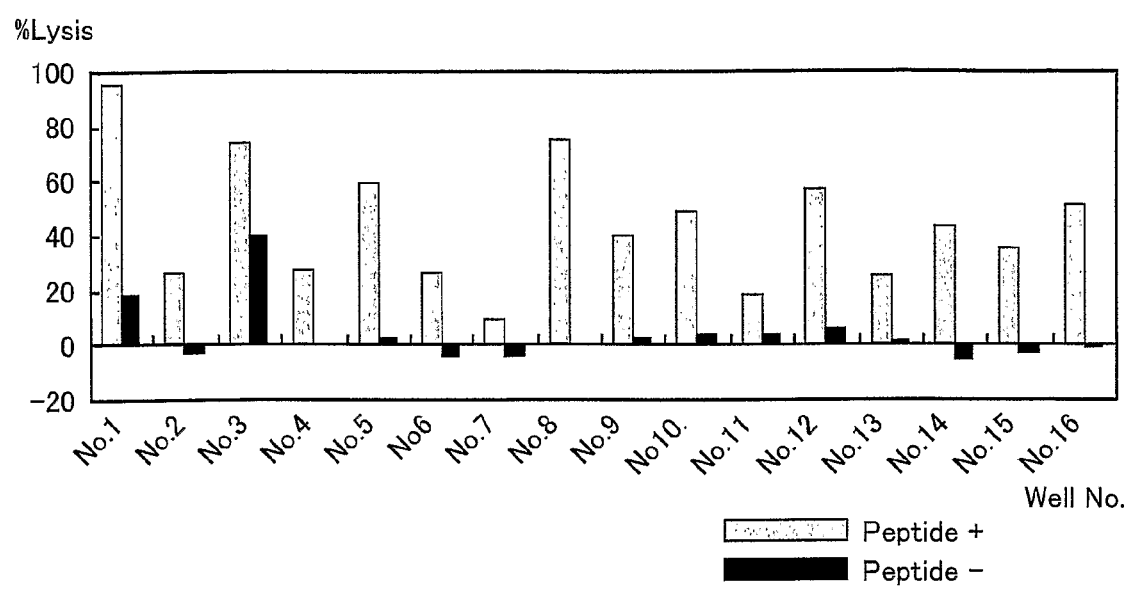
FIG. 5 depicts cytotoxic effect of CTL line induced by the 10-mer peptide TOM34-299. The CTL lines raised by the 10-mer peptide TOM34-299 showed peptide-specific cytotoxicity.

The CTL lines stimulated by the 10-mer peptide TOM34-299 (KLRQEVKQNL (SEQ ID NO; 7)) showed potent cytotoxic activity against the peptide-loaded target without showing any significant cytotoxic activity against targets not loaded with the peptide (FIG. 5). The CTL lines showed potent and antigen-specific cytotoxicity detectable at the E/T ratio of as low as 1.2 (FIG. 6).

Establishment of CTL Clones

Clones of CTLs were established by the limiting dilution of cultures of CTL lines followed by expansion as described in "Materials and Methods". CTL clones specific for TOM34-299 thus obtained contained those clones with very high cytolytic activities, with activities of the overall clones ranging 20% to 70% lysis at E/T ratio of 1.2 and 40% to >90% at E/T ratio of 10 (FIG. 7).

Cytotoxic Activity Against Colon Cancer Cell Lines Endogenously Expressing TOM34 as Targets The CTL clones raised against TOM34-299 peptide were examined for their ability to recognize and kill the tumor cells endogenously expressing TOM34. FIG. 8 shows the result with the two CTL clones raised against TOM34-299. Both of the two CTL clones showed potent cytotoxic activity against colon cancer cell lines DLD-1 and HT29, which express TOM34 as well as HLA-A24. On the other hand, neither of the two CTL clones showed any relevant cytotoxic activity against SNU-C2A colon cancer cell line, which expresses TOM34 but not HLA-A24 (FIG. 8).

Cold Target Inhibition Assay

Cold target inhibition assay was performed to confirm the specificity of the CTL lines. HT29 cells labeled by $^{51}$Cr were used as a hot target, while TISI cells with or without loaded peptide were used without $^{51}$Cr labeling as cold targets. Specific cell lysis against target HT29 cells was significantly inhibited when peptide-loaded cold target cells were added in the assay at various ratios but not inhibited at all by the addition of cold target cells without loaded peptide. The result is shown as a percentage of specific lysis at the Effector/Hot Target ratio of 20 (FIG. 9).

Homology Analysis of the Antigen Peptides

The CTL clones established against TOM34-299 showed very potent cytotoxic activity. This might mean that the sequence of this peptide is homologous to those derived from other molecules which are known to sensitize human immune system. To exclude this possibility, homology analysis was performed with the peptide sequences as a query using BLAST algorithm (on the world wide web at www.ncbi.nlm-.nih.gov/blast/blast.cgi) (Altschul S F, et al, Nucleic Acids Res. 1997; 25(17):3389-402; Altschul S F, et al., J Mol Biol. 1990; 215(3):403-10) and revealed no sequence with significant homology.

This indicates that the sequence of TOM34-299 is unique and there is little possibility, to our best knowledge, to raise unintended immunologic response to any unrelated molecule.

Blocking of CTL Activity by Antibodies that Bind to T-Cell Surface Antigens

To see whether the observed killing activity is mediated by the cytotoxic T-cells, effects of antibodies to the killing activity were investigated, using antibodies that neutralize the functions of T-cell surface antigens related to the CTL activity. CTL activity was clearly blocked by adding antibodies that recognize HLA Class I or CD8, and to a lesser extent by antibodies to HLA Class II or CD4, as shown in FIG. 10. This result shows that the cytotoxic activity of the T cell clone observed against HT29 colorectal carcinoma cells is the HLA-restricted killing activity of CD8-positive T lymphocytes.

Discussion

In the present invention, we have demonstrated that TOM34 is frequently up-regulated in CRCs and that it is abundantly expressed in normal testis and ovary and weakly expressed in the prostate, spleen, and colon, but rarely detected in other normal adult tissues examined.

One of romising therapeutic approaches is cancer immunotherapy, which includes T cell-mediated anti-tumor vaccination. Recognizing peptide antigens presented by molecules of the major histocompatibility complex (MHC), CD8$^+$ cytotoxic T cells targets cells displaying antigens. Since tumor cells originate from non-cancerous autologous cells, most of the tumor cells escape from immune surveillance. It is of great importance to identify antigens specifically expressed in cancer cells to apply cancer immunotherapy. Antigens are not expressed in the testis because of the lack of MHC class I molecules (Jassim A, et al., Eur J Immunol 19: 1215-1220, 1989). Hence, genes specifically expressed in cancer and testis should be target for immunotherapy. Since TOM34 is not abundantly expressed in normal organs except for testis and ovary, and is up-regulated in the majority of colon cancers, TOM34 may serve for a therapeutic target for CRC as a novel cancer-testis antigen.

Tom34 was initially considered to function as a component of the translocase for the import of proteins into mitochondria, because this protein showed sequence homology with yeast Tom protein (Nuttall S D, et al., DNA Cell Biol 16: 1067-1074, 1997). Although Tom34 was predicted to localize in an outer mitochondrial membrane, a recent study revealed that it was included in cytosol of Hela cells (Chun-Song Y & Henry W, Archives of Biochemistry and Biophysics 400: 105-110, 2002; Abhijit M, et al., Archives of Biochemistry and Biophysics 400: 97-104, 2002). Consistent with this data, we uncovered that subcellular localization of TOM34 was cytoplasm in CRC cells by immunohistochemical staining using anti-Tom34 polyclonal antibody. In another report, screening by using yeast two hybrid system identified Valosin-Containing Protein (VCP) and hsp90 as TOM34-interacting protein. VCP, an AAA (ATPases associated with a variety of cellular activities) family member also known as p97, forms a complex with the ubiquitinated IκBα and subunits of 26S proteosome, suggesting that VCP may be involved in the translocation of transcriptional factor NFκB to the nucleus by degradating IκBα (Dai R M, et al, J Biol Chem 273: 3562-3573, 1998). HSP90 is a molecular chaperone whose interaction is required for stability and function of a large number of molecules. Therefore, TOM34 could be stabilized by the binding with HSP90. Since HSP90 associates with oncogenic molecules such as Raf1, AKT and SMYD3, a number of HSP90 inhibitors have been developed for the treatment of human cancer. These inhibitors are assumed to cause severe adverse effects by hampering normal functional HSP90, because HSP90 is ubiquitously expressed in the majority of normal tissues.

In conclusion, TOM34 was up-regulated in CRCs but barely expressed in normal organs except the testis and ovary. Therefore, it is likely that the inhibition of TOM34 will not bring severe adverse effects on normal cells. In addition, suppression of TOM34 resulted in the inhibition of cell growth of cancer cells, suggesting that TOM34 play an essential role in their growth. These data implied that TOM34 is a promising target for immunotherapy and development anti-cancer drugs to human colorectal cancer.

In addition, identification of new TAAs, which induce potent and specific antitumor immune responses, warrants the further development of clinical application of peptide vaccination strategy in various types of cancer (Boon T & van der Bruggen P, J Exp Med. 1996; 183(3):725-9, van der Bruggen P, et al., Science. 1991; 254(5038):1643-7, Brichard V, et al., J Exp Med. 1993; 178(2):489-95., Kawakami Y, et al., J Exp Med. 1994; 180(1):347-52., Shichijo S, et al., J Exp Med. 1998; 187(3):277-88, Chen Y T, et al., Proc Natl Acad Sci USA. 1997; 94(5):1914-8., Harris C C., J Natl Cancer Inst. 1996; 88(20):1442-55., Butterfield L H, et al., Cancer Res. 1999; 59(13):3134-42., Vissers J L, et al., Cancer Res. 1999; 59(21):5554-9., van der Burg S H, et al., J Immunol. 1996; 156(9):3308-14., Tanaka F, et al., Cancer Res. 1997; 57(20):4465-8., Fujie T, et al., Int J Cancer. 1999; 80(2):169-72., Kikuchi M, et al., Int J Cancer. 1999; 81(3):459-66., Oiso M, et al., Int J Cancer. 1999; 81(3):387-94).

We analyzed the peptides derived from TOM34 as TAA epitopes restricted by HLA-A24, one of the frequent HLA allele in Japanese as well as in Caucasian population (Date Y, et al., Tissue Antigens, 1996; 47: 93-101., Kondo A, et al., J Immunol, 1995; 155: 4301-12, Kubo R T, et al., J Immunol, 1994; 152: 3913-24). In the present invention, we selected the candidates of HLA-A24-restricted epitope peptides derived from TOM34 using the information on their predicted binding affinities with HLA-4. After the in vitro stimulation of T cells by DCs loaded with these candidate peptides, CTLs were successfully established using a peptide TOM34-299 (KLRQEVKQNL) (SEQ ID NO; 7) that showed potent cytotoxic activity against the peptide-loaded TISI cells. Furthermore, CTL clones derived from these CTLs showed specific cytotoxicity also against colorectal carcinoma cell lines endogenously overexpressing TOM34 and positive for HLA-A24. The cytotoxic activities of these CTL clones were not displayed against the cell lines lacking expression of either HLA-A24 or the target TAA and are significantly inhibited by the cold target. These results strongly suggest that TOM34 is a novel TAA of colon cancer and that TOM34-299 is a specific epitope peptide of this TAA restricted by HLA-A24. Since this antigen is overexpressed in most cases of colon cancer and is associated with tumor cell proliferation, it appears to be a very good target to be used in immunotherapy against colon cancers.

Homology analysis of TOM34-299 showed that it does not have significant homology with the peptides derived from any known human gene products.

INDUSTRIAL APPLICABILITY

The gene-expression analysis of colon cancer described herein, obtained through a combination of laser-capture dissection and genome-wide cDNA microarray, has identified specific genes as targets for cancer prevention and therapy. Based on the expression of a subset of these differentially expressed genes, the present invention provides molecular diagnostic markers for identifying and detecting CRC.

The methods described herein are also useful in the identification of additional molecular targets for prevention, diagnosis and treatment of CRC. The data reported herein add to a comprehensive understanding of CRC, facilitate development of novel diagnostic strategies, and provide clues for identification of molecular targets for therapeutic drugs and preventative agents. Such information contributes to a more profound understanding of colon tumorigenesis, and provide indicators for developing novel strategies for diagnosis, treatment, and ultimately prevention of CRC.

For example, agents that block the expression of TOM34, or prevent its activity find therapeutic utility as anti-cancer agents, particularly anti-cancer agents for the treatment of CRC. Examples of such agents include antisense oligonucleotides, small interfering RNAs, and ribozymes against the TOM34 gene, and antibodies that recognize TOM34. Alternatively, identification of new TAAs, which induce potent and specific anti-tumor immune responses, warrants the further development of clinical application of peptide vaccination strategy in CRC.

Furthermore, while the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. Thus, the invention is intended to be defined not by the above description, but by the following claims and their equivalents.

The invention claimed is:

1. An isolated decapeptide consisting of the amino acid sequence of SEQ ID NO:7.

\* \* \* \* \*

UNITED STATES PATENT AND TRADEMARK OFFICE
CERTIFICATE OF CORRECTION

PATENT NO.        : 8,674,059 B2
APPLICATION NO.   : 11/913228
DATED             : March 18, 2014
INVENTOR(S)       : Nakamura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1039 days.

Signed and Sealed this
Twenty-ninth Day of September, 2015

Michelle K. Lee
*Director of the United States Patent and Trademark Office*